US 8,777,612 B2

(12) United States Patent
Suttin et al.

(10) Patent No.: US 8,777,612 B2
(45) Date of Patent: Jul. 15, 2014

(54) COMPONENTS FOR USE WITH A SURGICAL GUIDE FOR DENTAL IMPLANT PLACEMENT

(75) Inventors: Zachary B. Suttin, West Palm Beach, FL (US); T. Tait Robb, Stewart, FL (US); Bruce Berckmans, III, Palm Beach Gardens, FL (US); Ralph E. Goodman, West Palm Beach, FL (US); Theodore M. Powell, Palm Beach Gardens, FL (US)

(73) Assignee: Biomet 3i, LLC, Palm Beach Gardens, FL (US)

( * ) Notice: Subject to any disclaimer, the term of this patent is extended or adjusted under 35 U.S.C. 154(b) by 1156 days.

(21) Appl. No.: 12/271,517

(22) Filed: Nov. 14, 2008

(65) Prior Publication Data

US 2009/0130630 A1    May 21, 2009

Related U.S. Application Data

(60) Provisional application No. 61/003,407, filed on Nov. 16, 2007.

(51) Int. Cl.
*A61C 19/04* (2006.01)

(52) U.S. Cl.
USPC ........................................................... 433/72

(58) Field of Classification Search
USPC ................... 433/72, 172–175, 201.1, 75, 76
See application file for complete search history.

(56) References Cited

U.S. PATENT DOCUMENTS

| | | |
|---|---|---|
| 3,906,634 A | 9/1975 | Aspel |
| 3,919,772 A | 11/1975 | Lenczycki ................... 433/173 |
| 3,958,471 A | 5/1976 | Muller ........................... 82/1.11 |
| 4,011,602 A | 3/1977 | Rybicki et al. .............. 623/23.76 |
| 4,056,585 A | 11/1977 | Waltke ............................. 433/74 |
| 4,086,701 A | 5/1978 | Kawahara et al. ............ 433/174 |

(Continued)

FOREIGN PATENT DOCUMENTS

| | | | | |
|---|---|---|---|---|
| DE | 10029256 | 11/2000 | ............... | A61C 1/08 |
| WO | WO 94/26200 | 11/1994 | ............... | A61C 1/08 |

(Continued)

OTHER PUBLICATIONS

CAM StructSURE TM Precision Milled Bars Procedure & Lab. Manual by Implant Innovations, Inc—Rev. B Nov. 2005.*

(Continued)

*Primary Examiner* — Cris L Rodriguez
*Assistant Examiner* — Mirayda A Aponte
(74) *Attorney, Agent, or Firm* — Nixon Peabody LLP

(57) ABSTRACT

The present invention is a surgical guide for guiding the insertion of a dental implant into a desired location in a patient's mouth. The implant includes a non-rotational structure. The surgical guide includes a structure and a master tube. The structure has a negative impression surface to be fitted on and placed over gingival tissue, bone, and/or teeth in the patient's mouth. The structure includes an opening through which the dental implant is placed. The master tube is located at the opening. The master tube includes indicia for alignment with the non-rotational structure on the implant such that the non-rotational structure of the implant is at a known angular orientation with respect to the master tube. The present invention includes kits of various components used with the surgical guide and with the dental surgery using the surgical guide.

37 Claims, 18 Drawing Sheets

(56) References Cited

U.S. PATENT DOCUMENTS

| | | | |
|---|---|---|---|
| 4,177,562 A | 12/1979 | Miller et al. ................ 433/174 |
| 4,294,544 A | 10/1981 | Altschuler et al. ............ 356/610 |
| 4,306,862 A | 12/1981 | Knox .............................. 433/77 |
| 4,325,373 A | 4/1982 | Slivenko et al. |
| 4,341,312 A | 7/1982 | Scholer ........................ 211/70.6 |
| 4,364,381 A | 12/1982 | Sher et al. |
| 4,439,152 A | 3/1984 | Small |
| 4,543,953 A | 10/1985 | Slocum et al. |
| 4,547,157 A | 10/1985 | Driskell ........................ 433/173 |
| 4,571,180 A | 2/1986 | Kulick |
| 4,611,288 A | 9/1986 | Duret ............................ 700/163 |
| 4,624,673 A | 11/1986 | Meyer ........................... 433/173 |
| 4,663,720 A | 5/1987 | Duret ............................ 700/163 |
| 4,713,004 A | 12/1987 | Linkow et al. ................ 433/174 |
| 4,756,689 A | 7/1988 | Lundgren et al. |
| 4,758,161 A | 7/1988 | Niznick ......................... 433/173 |
| 4,767,331 A | 8/1988 | Hoe ................................ 433/213 |
| 4,772,204 A | 9/1988 | Soderberg .................... 433/174 |
| 4,821,200 A | 4/1989 | Oberg ........................... 700/182 |
| 4,842,518 A | 6/1989 | Linkow et al. ................ 433/174 |
| 4,850,870 A | 7/1989 | Lazzara et al. ............... 433/174 |
| 4,850,873 A | 7/1989 | Lazzara et al. ............... 433/220 |
| 4,854,872 A | 8/1989 | Detsch .......................... 433/173 |
| 4,856,994 A | 8/1989 | Lazzara et al. ............... 433/173 |
| 4,872,839 A | 10/1989 | Brajnovic |
| 4,906,191 A | 3/1990 | Soderberg .................... 433/213 |
| 4,906,420 A | 3/1990 | Brajnovic et al. |
| 4,931,016 A | 6/1990 | Sillard |
| 4,935,635 A | 6/1990 | O'Harra ....................... 250/559.06 |
| 4,961,674 A | 10/1990 | Wang et al. |
| 4,964,770 A | 10/1990 | Steinbichler ................. 433/223 |
| 4,986,753 A | 1/1991 | Sellers |
| 4,988,297 A | 1/1991 | Lazzara et al. |
| 4,998,881 A | 3/1991 | Lauks |
| 5,000,685 A | 3/1991 | Brajnovic |
| 5,006,069 A | 4/1991 | Lazzara et al. ............... 433/173 |
| 5,015,183 A | 5/1991 | Fenick |
| 5,015,186 A | 5/1991 | Detsch |
| 5,030,096 A | 7/1991 | Hurson et al. ................ 433/173 |
| 5,035,619 A | 7/1991 | Daftary ......................... 433/173 |
| 5,040,982 A | 8/1991 | Stefan-Dogar |
| 5,040,983 A | 8/1991 | Binon ............................ 433/173 |
| 5,064,375 A | 11/1991 | Jorneus ......................... 433/229 |
| 5,071,351 A | 12/1991 | Green, Jr. et al. ............. 433/173 |
| 5,073,111 A | 12/1991 | Daftary ......................... 433/173 |
| 5,087,200 A | 2/1992 | Brajnovic et al. |
| 5,100,323 A | 3/1992 | Friedman et al. ............. 433/173 |
| 5,104,318 A | 4/1992 | Piche et al. ................... 433/174 |
| 5,106,300 A | 4/1992 | Voitik ............................ 433/173 |
| 5,122,059 A | 6/1992 | Durr et al. ..................... 433/173 |
| 5,125,839 A | 6/1992 | Ingber et al. .................. 433/169 |
| 5,125,841 A | 6/1992 | Carlsson et al. .............. 433/213 |
| 5,133,660 A | 7/1992 | Fenick |
| 5,135,395 A | 8/1992 | Marlin .......................... 433/174 |
| 5,145,371 A | 9/1992 | Jorneus ......................... 433/173 |
| 5,145,372 A | 9/1992 | Daftary ......................... 433/173 |
| 5,176,516 A | 1/1993 | Koizumi |
| 5,188,800 A | 2/1993 | Green, Jr. et al. ................ 134/1 |
| 5,195,892 A | 3/1993 | Gersberg ...................... 433/174 |
| 5,205,745 A | 4/1993 | Kamiya et al. ............... 433/173 |
| 5,209,659 A | 5/1993 | Friedman et al. ............. 433/173 |
| 5,209,666 A | 5/1993 | Balfour et al. ................ 433/173 |
| 5,213,502 A | 5/1993 | Daftary ......................... 433/172 |
| 5,221,204 A * | 6/1993 | Kruger et al. ................. 433/173 |
| 5,237,998 A | 8/1993 | Duret et al. ................... 600/476 |
| 5,246,370 A | 9/1993 | Coatoam |
| 5,257,184 A | 10/1993 | Mushabac ....................... 433/75 |
| 5,281,140 A | 1/1994 | Niznick ......................... 433/172 |
| 5,286,195 A | 2/1994 | Clostermann ................ 433/173 |
| 5,286,196 A | 2/1994 | Brajnovic et al. |
| 5,292,252 A | 3/1994 | Nickerson et al. ............ 433/173 |
| 5,297,963 A | 3/1994 | Dafatry ......................... 433/172 |
| 5,302,125 A | 4/1994 | Kownacki et al. |
| 5,312,254 A | 5/1994 | Rosenlicht ................... 433/173 |
| 5,312,409 A | 5/1994 | McLaughlin et al. |
| 5,316,476 A | 5/1994 | Krauser ........................ 433/173 |
| 5,320,529 A | 6/1994 | Pompa |
| 5,328,371 A | 7/1994 | Hund et al. |
| 5,334,024 A | 8/1994 | Niznick ......................... 433/173 |
| 5,336,090 A | 8/1994 | Wilson, Jr. et al. ........... 433/172 |
| 5,338,196 A | 8/1994 | Beaty et al. ................... 433/172 |
| 5,338,198 A | 8/1994 | Wu et al. ....................... 433/213 |
| 5,343,391 A | 8/1994 | Mushabac ....................... 433/76 |
| 5,344,457 A | 9/1994 | Pilliar et al. .................... 606/60 |
| 5,350,297 A | 9/1994 | Cohen |
| 5,359,511 A | 10/1994 | Schroeder et al. .............. 433/75 |
| 5,362,234 A | 11/1994 | Salazar et al. ................ 433/169 |
| 5,362,235 A | 11/1994 | Daftary ......................... 433/172 |
| 5,368,483 A | 11/1994 | Sutter et al. ................... 433/173 |
| 5,370,692 A | 12/1994 | Fink et al. ..................... 128/898 |
| 5,372,502 A | 12/1994 | Massen et al. ................ 433/215 |
| 5,386,292 A | 1/1995 | Massen et al. ................ 356/603 |
| 5,413,481 A | 5/1995 | Goppel et al. ................ 433/214 |
| 5,417,569 A | 5/1995 | Perisse |
| 5,417,570 A | 5/1995 | Zuest et al. ................... 433/177 |
| 5,419,702 A | 5/1995 | Beaty et al. ................... 433/214 |
| 5,431,567 A | 7/1995 | Daftary ......................... 433/172 |
| 5,437,551 A | 8/1995 | Chalifoux ..................... 433/173 |
| 5,440,393 A | 8/1995 | Wenz ............................ 356/611 |
| 5,452,219 A | 9/1995 | Dehoff et al. ................. 700/163 |
| 5,458,488 A | 10/1995 | Chalifoux ..................... 433/173 |
| 5,476,382 A | 12/1995 | Daftary ......................... 433/172 |
| 5,476,383 A | 12/1995 | Beaty et al. ................... 433/214 |
| 5,492,471 A | 2/1996 | Singer ........................... 433/172 |
| 5,516,288 A | 5/1996 | Sichler et al. |
| 5,527,182 A | 6/1996 | Willoughby |
| 5,533,898 A | 7/1996 | Mena ............................ 433/173 |
| 5,538,426 A | 7/1996 | Harding et al. ............... 433/172 |
| 5,547,377 A | 8/1996 | Daftary ......................... 433/172 |
| 5,556,278 A | 9/1996 | Meitner |
| 5,564,921 A | 10/1996 | Marlin .......................... 433/172 |
| 5,564,924 A | 10/1996 | Kwan ............................ 433/173 |
| 5,569,578 A | 10/1996 | Mushabac ..................... 433/215 |
| 5,575,656 A | 11/1996 | Hajjar |
| 5,580,244 A | 12/1996 | White .............................. 433/37 |
| 5,580,246 A | 12/1996 | Fried et al. |
| 5,595,703 A | 1/1997 | Swaelens ...................... 264/401 |
| 5,613,852 A | 3/1997 | Bavitz |
| 5,630,717 A | 5/1997 | Zuest et al. |
| 5,636,986 A | 6/1997 | Pezeshkian |
| 5,651,675 A | 7/1997 | Singer ........................... 433/172 |
| 5,652,709 A | 7/1997 | Andersson .................... 700/161 |
| 5,658,147 A | 8/1997 | Phimmasone ................ 433/213 |
| 5,662,476 A | 9/1997 | Ingber et al. |
| 5,674,069 A | 10/1997 | Osorio .......................... 433/172 |
| 5,674,071 A | 10/1997 | Beaty et al. ................... 433/172 |
| 5,674,073 A | 10/1997 | Ingber et al. .................. 433/213 |
| 5,681,167 A | 10/1997 | Lazarof ......................... 433/174 |
| 5,685,715 A | 11/1997 | Beaty et al. ................... 433/173 |
| 5,688,283 A | 11/1997 | Knapp |
| 5,704,936 A | 1/1998 | Mazel |
| 5,718,579 A | 2/1998 | Kennedy |
| 5,725,376 A | 3/1998 | Poirier |
| 5,733,124 A | 3/1998 | Kwan |
| 5,741,215 A | 4/1998 | D'Urso ......................... 600/407 |
| 5,743,916 A | 4/1998 | Greenberg et al. |
| 5,759,036 A | 6/1998 | Hinds ............................ 433/214 |
| 5,762,125 A | 6/1998 | Mastrorio ...................... 164/4.1 |
| 5,762,500 A | 6/1998 | Lazarof |
| 5,768,134 A | 6/1998 | Swaelens et al. |
| 5,769,636 A | 6/1998 | Di Sario |
| 5,791,902 A | 8/1998 | Lauks |
| 5,800,168 A | 9/1998 | Cascione et al. |
| 5,813,858 A | 9/1998 | Singer ........................... 433/173 |
| 5,823,778 A | 10/1998 | Schmitt ........................ 433/214 |
| 5,842,859 A | 12/1998 | Palacci |
| 5,846,079 A | 12/1998 | Knode |
| 5,851,115 A | 12/1998 | Carlsson et al. .............. 433/215 |
| 5,857,853 A | 1/1999 | van Nifterick et al. ....... 433/213 |
| 5,871,358 A | 2/1999 | Ingber et al. |
| 5,873,722 A | 2/1999 | Lazzara et al. ............... 433/173 |
| 5,876,204 A | 3/1999 | Day et al. |
| 5,885,078 A | 3/1999 | Cagna et al. |
| 5,888,034 A | 3/1999 | Greenberg |

(56) References Cited

U.S. PATENT DOCUMENTS

| | | | |
|---|---|---|---|
| 5,904,483 A | 5/1999 | Wade | |
| 5,915,962 A | 6/1999 | Rosenlicht | |
| 5,927,982 A | 7/1999 | Kruger | |
| 5,938,443 A | 8/1999 | Lazzara et al. | 433/173 |
| 5,954,769 A | 9/1999 | Rosenlicht | |
| 5,964,591 A | 10/1999 | Beaty et al. | |
| 5,967,777 A | 10/1999 | Klein et al. | |
| 5,984,681 A | 11/1999 | Huang | |
| 5,989,025 A | 11/1999 | Conley | |
| 5,989,029 A | 11/1999 | Osorio et al. | 433/173 |
| 5,989,258 A | 11/1999 | Hattori | |
| 5,997,681 A | 12/1999 | Kinzie | 156/263 |
| 6,000,939 A | 12/1999 | Ray et al. | |
| 6,008,905 A | 12/1999 | Breton et al. | 356/402 |
| 6,068,479 A | 5/2000 | Kwan | |
| 6,099,311 A | 8/2000 | Wagner et al. | |
| 6,099,313 A | 8/2000 | Dorken et al. | |
| 6,099,314 A | 8/2000 | Kopelman et al. | 433/213 |
| 6,120,293 A | 9/2000 | Lazzara et al. | 433/173 |
| 6,129,548 A | 10/2000 | Lazzara et al. | 433/172 |
| 6,135,773 A | 10/2000 | Lazzara | |
| 6,142,782 A | 11/2000 | Lazarof | |
| 6,174,168 B1 | 1/2001 | Dehoff et al. | 433/202.1 |
| 6,175,413 B1 | 1/2001 | Lucas | 356/614 |
| 6,190,169 B1 | 2/2001 | Bluemli et al. | |
| 6,197,410 B1 | 3/2001 | Vallittu et al. | |
| 6,200,125 B1 | 3/2001 | Akutagawa | 425/462 |
| 6,206,693 B1 | 3/2001 | Hultgren | 433/38 |
| 6,210,162 B1 | 4/2001 | Chishti et al. | 433/213 |
| 6,217,334 B1 | 4/2001 | Hultgren | 433/215 |
| 6,227,859 B1 | 5/2001 | Sutter | |
| 6,283,753 B1 | 9/2001 | Willoughby | 433/172 |
| 6,287,119 B1 | 9/2001 | van Nifterick et al. | |
| 6,296,483 B1 | 10/2001 | Champleboux | |
| 6,319,000 B1 | 11/2001 | Branemark | |
| 6,322,728 B1 | 11/2001 | Brodkin et al. | 264/19 |
| 6,382,975 B1 | 5/2002 | Poirier | |
| 6,402,707 B1 | 6/2002 | Ernst | 600/590 |
| 6,488,503 B1 | 12/2002 | Lichkus et al. | 433/202 |
| 6,497,574 B1 | 12/2002 | Miller | 433/213 |
| 6,540,784 B2 | 4/2003 | Barlow et al. | 623/16.11 |
| 6,568,936 B2 | 5/2003 | MacDougald et al. | |
| 6,575,751 B1 | 6/2003 | Lehmann et al. | 433/223 |
| 6,594,539 B1 | 7/2003 | Geng | 700/117 |
| 6,610,079 B1 | 8/2003 | Li et al. | |
| 6,619,958 B2 | 9/2003 | Beaty et al. | 433/173 |
| 6,629,840 B2 | 10/2003 | Chishti et al. | 433/24 |
| 6,634,883 B2 | 10/2003 | Ranalli | |
| 6,648,640 B2 | 11/2003 | Rubbert et al. | 433/24 |
| 6,671,539 B2 | 12/2003 | Gateno et al. | 600/426 |
| 6,672,870 B2 | 1/2004 | Knapp | |
| 6,688,887 B2 | 2/2004 | Morgan | |
| 6,691,764 B2 | 2/2004 | Embert et al. | 164/4.1 |
| 6,743,491 B2 | 6/2004 | Cirincione et al. | |
| 6,755,652 B2 | 6/2004 | Nanni | |
| 6,772,026 B2 | 8/2004 | Bradbury et al. | 700/98 |
| 6,776,614 B2 | 8/2004 | Wiechmann et al. | 433/24 |
| 6,783,359 B2 | 8/2004 | Kapit | |
| 6,790,040 B2 | 9/2004 | Amber et al. | 433/173 |
| 6,793,491 B2 | 9/2004 | Klein et al. | |
| 6,808,659 B2 | 10/2004 | Schulman et al. | 264/16 |
| 6,814,575 B2 * | 11/2004 | Poirier | 433/75 |
| 6,821,462 B2 | 11/2004 | Schulman et al. | 264/16 |
| 6,829,498 B2 | 12/2004 | Kipke et al. | 600/378 |
| D503,804 S | 4/2005 | Phleps et al. | |
| 6,882,894 B2 | 4/2005 | Durbin et al. | 700/118 |
| 6,885,464 B1 | 4/2005 | Pfeiffer et al. | |
| 6,902,401 B2 | 6/2005 | Jorneus | |
| 6,913,463 B2 | 7/2005 | Blacklock | |
| 6,926,442 B2 | 8/2005 | Stöckl | |
| 6,926,525 B1 | 8/2005 | Ronrig et al. | |
| 6,939,489 B2 | 9/2005 | Moszner et al. | 264/16 |
| 6,942,699 B2 | 9/2005 | Stone et al. | |
| 6,953,383 B2 | 10/2005 | Rothenberger | |
| 6,957,118 B2 | 10/2005 | Kopelman et al. | 700/118 |
| 6,966,772 B2 | 11/2005 | Malin et al. | |
| 6,970,760 B2 | 11/2005 | Wolf et al. | 700/163 |
| 6,971,877 B2 | 12/2005 | Harter | |
| 6,994,549 B2 | 2/2006 | Brodkin et al. | 433/202.1 |
| 7,010,150 B1 | 3/2006 | Pfeiffer et al. | |
| 7,010,153 B2 | 3/2006 | Zimmermann | |
| 7,012,988 B2 | 3/2006 | Adler et al. | |
| 7,018,207 B2 | 3/2006 | Prestipino | |
| 7,021,934 B2 | 4/2006 | Aravena | |
| 7,029,275 B2 | 4/2006 | Rubbert et al. | 433/24 |
| 7,044,735 B2 | 5/2006 | Malin | |
| 7,056,115 B2 | 6/2006 | Phan et al. | 433/24 |
| 7,056,472 B1 | 6/2006 | Behringer | |
| 7,059,856 B2 | 6/2006 | Marotta | |
| 7,066,736 B2 | 6/2006 | Kumar et al. | |
| 7,084,868 B2 | 8/2006 | Farag et al. | |
| 7,086,860 B2 | 8/2006 | Schuman et al. | |
| 7,097,451 B2 | 8/2006 | Tang | |
| 7,104,795 B2 | 9/2006 | Dadi | |
| 7,110,844 B2 | 9/2006 | Kopelman et al. | 700/118 |
| 7,112,065 B2 | 9/2006 | Kopelman et al. | 433/213 |
| 7,118,375 B2 | 10/2006 | Durbin et al. | 433/68 |
| D532,991 S | 12/2006 | Gozzi | |
| 7,153,132 B2 | 12/2006 | Tedesco | |
| 7,153,135 B1 | 12/2006 | Thomas | 433/213 |
| 7,163,443 B2 | 1/2007 | Basler et al. | |
| 7,175,434 B2 | 2/2007 | Brajnovic | |
| 7,175,435 B2 | 2/2007 | Andersson et al. | |
| 7,178,731 B2 | 2/2007 | Basler | |
| 7,214,062 B2 | 5/2007 | Morgan | |
| 7,220,124 B2 | 5/2007 | Taub et al. | 433/213 |
| 7,228,191 B2 | 6/2007 | Hofmeister et al. | 700/98 |
| 7,236,842 B2 | 6/2007 | Kopelman et al. | 700/98 |
| 7,281,927 B2 | 10/2007 | Marotta | |
| 7,286,954 B2 | 10/2007 | Kopelman et al. | 702/152 |
| 7,303,420 B2 | 12/2007 | Huch et al. | |
| 7,319,529 B2 | 1/2008 | Babayoff | 356/601 |
| 7,322,746 B2 | 1/2008 | Beckhaus et al. | |
| 7,322,824 B2 | 1/2008 | Schmitt | 433/215 |
| 7,324,680 B2 | 1/2008 | Zimmermann | |
| 7,329,122 B1 | 2/2008 | Scott | |
| 7,333,874 B2 | 2/2008 | Taub et al. | 700/117 |
| 7,335,876 B2 | 2/2008 | Eiff et al. | |
| D565,184 S | 3/2008 | Royzen | |
| 7,367,801 B2 | 5/2008 | Saliger | |
| 7,379,584 B2 | 5/2008 | Rubbert et al. | 382/154 |
| D571,471 S | 6/2008 | Stöckl | |
| 7,381,191 B2 | 6/2008 | Fallah | |
| 7,383,094 B2 | 6/2008 | Kopelman et al. | 700/118 |
| D575,747 S | 8/2008 | Abramovich et al. | |
| 7,421,608 B2 | 9/2008 | Schron | |
| 7,429,175 B2 | 9/2008 | Gittelson | |
| 7,435,088 B2 | 10/2008 | Brajnovic | |
| 7,476,100 B2 | 1/2009 | Kuo | 433/6 |
| 7,481,647 B2 | 1/2009 | Sambu et al. | 425/436 |
| 7,488,174 B2 | 2/2009 | Kopelman et al. | 433/213 |
| 7,497,619 B2 | 3/2009 | Stoeckl | |
| 7,497,983 B2 | 3/2009 | Khan et al. | 264/673 |
| 7,520,747 B2 | 4/2009 | Stonisch | |
| 7,522,764 B2 | 4/2009 | Schwotzer | |
| 7,534,266 B2 | 5/2009 | Kluger | |
| 7,536,234 B2 | 5/2009 | Kopelman et al. | 700/118 |
| 7,545,372 B2 | 6/2009 | Kopelman et al. | 345/419 |
| 7,551,760 B2 | 6/2009 | Scharlack et al. | |
| 7,555,403 B2 | 6/2009 | Kopelman et al. | 702/152 |
| 7,556,496 B2 | 7/2009 | Cinader, Jr. et al. | 433/24 |
| 7,559,692 B2 | 7/2009 | Beckhaus et al. | |
| 7,563,397 B2 | 7/2009 | Schulman et al. | 264/16 |
| D597,769 S | 8/2009 | Richter et al. | |
| 7,572,058 B2 | 8/2009 | Pruss et al. | |
| 7,572,125 B2 | 8/2009 | Brajnovic | |
| 7,574,025 B2 | 8/2009 | Feldman | 382/128 |
| 7,578,673 B2 | 8/2009 | Wen et al. | 433/24 |
| 7,580,502 B2 | 8/2009 | Dalpiaz et al. | |
| 7,581,951 B2 | 9/2009 | Lehmann et al. | |
| 7,582,855 B2 | 9/2009 | Pfeiffer | |
| 7,628,537 B2 | 12/2009 | Schulze-Ganzlin | |
| 7,632,097 B2 | 12/2009 | De Clerck | 433/215 |
| 7,653,455 B2 | 1/2010 | Cinader, Jr. | |

(56) References Cited

U.S. PATENT DOCUMENTS

| | | | |
|---|---|---|---|
| 7,654,823 B2 | 2/2010 | Dadi | |
| 7,655,586 B1 | 2/2010 | Brodkin et al. | 501/103 |
| 7,658,610 B2 | 2/2010 | Knopp | 433/24 |
| 7,661,956 B2 * | 2/2010 | Powell et al. | 433/172 |
| 7,665,989 B2 | 2/2010 | Brajnovic et al. | |
| 7,679,723 B2 | 3/2010 | Schwotzer | |
| 7,687,754 B2 | 3/2010 | Eiff et al. | |
| 7,689,308 B2 | 3/2010 | Holzner et al. | |
| D614,210 S | 4/2010 | Basler et al. | |
| 7,698,014 B2 | 4/2010 | Dunne et al. | |
| 7,774,084 B2 | 8/2010 | Cinader, Jr. | |
| 7,780,907 B2 | 8/2010 | Schmidt et al. | |
| 7,785,007 B2 | 8/2010 | Stoeckl | |
| 7,787,132 B2 | 8/2010 | Körner et al. | |
| 7,796,811 B2 | 9/2010 | Orth et al. | |
| 7,798,708 B2 | 9/2010 | Erhardt et al. | |
| 7,801,632 B2 | 9/2010 | Orth et al. | |
| 7,815,371 B2 | 10/2010 | Schulze-Ganzlin | |
| 7,824,181 B2 | 11/2010 | Sers | |
| D629,908 S | 12/2010 | Jerger et al. | |
| 7,855,354 B2 | 12/2010 | Eiff | |
| 7,865,261 B2 | 1/2011 | Pfeiffer | |
| 7,876,877 B2 | 1/2011 | Stockl | |
| 7,901,209 B2 | 3/2011 | Saliger et al. | |
| 7,982,731 B2 | 7/2011 | Orth et al. | |
| 7,985,119 B2 | 7/2011 | Basler et al. | |
| 7,986,415 B2 | 7/2011 | Thiel et al. | |
| 8,026,943 B2 | 9/2011 | Weber et al. | |
| 8,038,440 B2 * | 10/2011 | Swaelens et al. | 433/76 |
| 8,047,895 B2 | 11/2011 | Basler | |
| 8,057,912 B2 | 11/2011 | Basler et al. | |
| 8,062,034 B2 | 11/2011 | Hanisch et al. | |
| 8,083,522 B2 | 12/2011 | Karkar et al. | |
| 8,105,081 B2 * | 1/2012 | Bavar | 433/75 |
| 2001/0008751 A1 | 7/2001 | Chishti et al. | |
| 2001/0034010 A1 | 10/2001 | MacDougald et al. | 433/223 |
| 2002/0010568 A1 | 1/2002 | Rubbert et al. | 703/6 |
| 2002/0028418 A1 | 3/2002 | Farag et al. | 433/29 |
| 2002/0160337 A1 | 10/2002 | Klein et al. | |
| 2002/0167100 A1 | 11/2002 | Moszner et al. | 264/16 |
| 2003/0130605 A1 | 7/2003 | Besek | |
| 2003/0222366 A1 | 12/2003 | Stangel et al. | 264/16 |
| 2004/0029074 A1 | 2/2004 | Brajnovic | |
| 2004/0048227 A1 | 3/2004 | Brajnovic | |
| 2004/0219477 A1 | 11/2004 | Harter | |
| 2004/0219479 A1 | 11/2004 | Malin et al. | |
| 2004/0219490 A1 | 11/2004 | Gartner et al. | 433/218 |
| 2004/0220691 A1 | 11/2004 | Hofmeister et al. | 700/98 |
| 2004/0243481 A1 | 12/2004 | Bradbury et al. | 705/26 |
| 2004/0259051 A1 | 12/2004 | Brajnovic | |
| 2005/0023710 A1 | 2/2005 | Brodkin et al. | 264/16 |
| 2005/0056350 A1 | 3/2005 | Dolabdjian et al. | 148/512 |
| 2005/0070782 A1 | 3/2005 | Brodkin | 600/407 |
| 2005/0084144 A1 | 4/2005 | Feldman | 382/128 |
| 2005/0100861 A1 | 5/2005 | Choi | |
| 2005/0170311 A1 * | 8/2005 | Tardieu et al. | 433/76 |
| 2005/0271996 A1 | 12/2005 | Sporbert et al. | 433/24 |
| 2005/0277089 A1 | 12/2005 | Brajnovic | |
| 2005/0277090 A1 | 12/2005 | Anderson et al. | |
| 2005/0277091 A1 | 12/2005 | Andersson et al. | |
| 2005/0282106 A1 | 12/2005 | Sussman et al. | |
| 2005/0283065 A1 | 12/2005 | Babayoff | 600/407 |
| 2006/0006561 A1 | 1/2006 | Brajnovic | |
| 2006/0008763 A1 | 1/2006 | Brajnovic | |
| 2006/0008770 A1 | 1/2006 | Brajnovic et al. | |
| 2006/0093988 A1 | 5/2006 | Swaelens et al. | |
| 2006/0094951 A1 | 5/2006 | Dean et al. | 600/407 |
| 2006/0127848 A1 | 6/2006 | Sogo et al. | |
| 2006/0210949 A1 | 9/2006 | Stoop | |
| 2006/0263741 A1 | 11/2006 | Imgrund et al. | 433/24 |
| 2006/0281041 A1 | 12/2006 | Rubbert et al. | 433/24 |
| 2007/0015111 A1 | 1/2007 | Kopelman et al. | 433/213 |
| 2007/0031790 A1 | 2/2007 | Raby et al. | 433/213 |
| 2007/0065777 A1 | 3/2007 | Becker | |
| 2007/0077532 A1 | 4/2007 | Harter | |
| 2007/0092854 A1 | 4/2007 | Powell et al. | 433/213 |
| 2007/0141525 A1 | 6/2007 | Cinader, Jr. et al. | 433/23 |
| 2007/0211081 A1 | 9/2007 | Quadling et al. | 345/632 |
| 2007/0218426 A1 | 9/2007 | Quadling et al. | 433/223 |
| 2007/0269769 A1 | 11/2007 | Marchesi | 433/215 |
| 2007/0281277 A1 | 12/2007 | Brajnovic | |
| 2008/0038692 A1 | 2/2008 | Andersson et al. | |
| 2008/0044794 A1 | 2/2008 | Brajnovic | |
| 2008/0057467 A1 | 3/2008 | Gittelson | |
| 2008/0070181 A1 | 3/2008 | Abolfathi et al. | 433/6 |
| 2008/0085489 A1 | 4/2008 | Schmitt | |
| 2008/0090210 A1 | 4/2008 | Brajnovic | |
| 2008/0114371 A1 | 5/2008 | Kluger | |
| 2008/0118895 A1 | 5/2008 | Brajnovic | |
| 2008/0124676 A1 | 5/2008 | Marotta | |
| 2008/0153060 A1 * | 6/2008 | De Moyer | 433/173 |
| 2008/0153061 A1 | 6/2008 | Marcello | 433/173 |
| 2008/0153065 A1 | 6/2008 | Brajnovic | |
| 2008/0153069 A1 | 6/2008 | Holzner et al. | 433/223 |
| 2008/0176189 A1 | 7/2008 | Stonisch | |
| 2008/0206714 A1 | 8/2008 | Schmitt | 433/215 |
| 2008/0241798 A1 | 10/2008 | Holzner et al. | 433/223 |
| 2008/0261165 A1 | 10/2008 | Steingart et al. | 433/24 |
| 2008/0300716 A1 | 12/2008 | Kopelman et al. | 700/182 |
| 2009/0017418 A1 | 1/2009 | Gittelson | |
| 2009/0026643 A1 | 1/2009 | Wiest et al. | 264/16 |
| 2009/0042167 A1 | 2/2009 | Van Der Zel | 433/215 |
| 2009/0081616 A1 | 3/2009 | Pfeiffer | 433/215 |
| 2009/0087817 A1 | 4/2009 | Jansen et al. | 433/223 |
| 2009/0092948 A1 | 4/2009 | Gantes | |
| 2009/0098510 A1 | 4/2009 | Zhang | 433/201.1 |
| 2009/0098511 A1 | 4/2009 | Zhang | 433/201.1 |
| 2009/0123045 A1 | 5/2009 | Quadling et al. | 382/128 |
| 2009/0123887 A1 | 5/2009 | Brajnovic | |
| 2009/0187393 A1 | 7/2009 | Van Lierde et al. | |
| 2009/0220134 A1 | 9/2009 | Cahill et al. | |
| 2009/0220916 A1 | 9/2009 | Fisker et al. | 433/201.1 |
| 2009/0220917 A1 | 9/2009 | Jensen | 433/202.1 |
| 2009/0239197 A1 | 9/2009 | Brajnovic | |
| 2009/0239200 A1 | 9/2009 | Brajnovic et al. | |
| 2009/0253097 A1 | 10/2009 | Brajnovic | |
| 2009/0287332 A1 | 11/2009 | Adusumilli et al. | 700/98 |
| 2009/0298009 A1 | 12/2009 | Brajnovic | |
| 2009/0298017 A1 | 12/2009 | Boerjes et al. | 433/214 |
| 2009/0317763 A1 | 12/2009 | Brajnovic | |
| 2009/0325122 A1 | 12/2009 | Brajnovic et al. | |
| 2010/0009314 A1 | 1/2010 | Tardieu et al. | |
| 2010/0028827 A1 | 2/2010 | Andersson et al. | |
| 2010/0038807 A1 | 2/2010 | Brodkin et al. | 264/17 |
| 2010/0075275 A1 | 3/2010 | Brainovic | |
| 2010/0092904 A1 | 4/2010 | Esposti et al. | |
| 2010/0173260 A1 | 7/2010 | Sogo et al. | |
| 2010/0280798 A1 | 11/2010 | Pattijn et al. | |
| 2011/0008751 A1 | 1/2011 | Pettersson | |
| 2011/0060558 A1 | 3/2011 | Pettersson | |
| 2011/0191081 A1 | 8/2011 | Malfliet et al. | |
| 2011/0275032 A1 | 11/2011 | Tardieu et al. | |
| 2012/0010740 A1 | 1/2012 | Swaelens et al. | |
| 2012/0164593 A1 | 6/2012 | Bavar | 433/29 |
| 2012/0164893 A1 | 6/2012 | Misuzuka et al. | 439/692 |

FOREIGN PATENT DOCUMENTS

| | | | |
|---|---|---|---|
| WO | 9932045 | 7/1999 | |
| WO | WO 00/08415 | 2/2000 | A61B 5/107 |
| WO | 0158379 A1 | 8/2001 | |
| WO | 02053055 A1 | 7/2002 | |
| WO | WO 03/024352 | 3/2003 | A61C 8/00 |
| WO | WO 2004/030565 | 4/2004 | A61C 13/00 |
| WO | WO 2004075771 A1 * | 9/2004 | |
| WO | 2004075771 A1 | 10/2004 | |
| WO | WO 2004/087000 | 10/2004 | A61C 13/00 |
| WO | WO2004/098435 | 11/2004 | |
| WO | 2006014130 A1 | 2/2006 | |
| WO | 2006062459 A1 | 6/2006 | |
| WO | WO 2006082198 A1 * | 8/2006 | |
| WO | 2006082198 A1 | 10/2006 | |
| WO | WO2007/033157 | 3/2007 | |
| WO | 2007104842 A1 | 9/2007 | |

(56) References Cited

FOREIGN PATENT DOCUMENTS

| WO | 2007129955 A1 | 11/2007 |
| WO | WO 2007129955 A1 * | 11/2007 |
| WO | WO2008/057955 | 5/2008 |
| WO | WO2008/083857 | 7/2008 |

OTHER PUBLICATIONS

Clinical Perspectives vol. 6, Issue 3—"Intro. The Navigator System for Minimally Invasive Computed Tomograpy Guided Surgery" by A. Rosenfeld, R. Mecall and P. Ostman—Biomet 3i—Rev. A Oct. 2007.*
"SurgiGuide Cookbook Drill Guides for Every Case Scenario" by Simplant/Materialise Medical Rev. Mar. 17, 2006.*
BIOMET3i Navigator™; "Navigator™ System for CT Guided Surgery Manual", pp. 1-26, Oct. 2007.
Imaterialise Medical; "Surgical Guide Cookbook, Drill Guides for Every Scenario"; pp. 1-87, Date unknown.
European Search Report dated Apr. 24, 2009 for 08019960.7.
Imaterialise Medical; :Surgical Guide Cookbook, Brill Guides for Every Scenario; pp. 1-87, Date unknown.

* cited by examiner

COMPONENTS FOR USE WITH A SURGICAL GUIDE FOR DENTAL IMPLANT PLACEMENT

CROSS REFERENCE TO RELATED APPLICATIONS

This application claims priority to U.S. Provisional Application No. 61/003,407 filed Nov. 16, 2007, the contents of which are incorporated entirely herein by reference.

BACKGROUND OF THE INVENTION

The present invention relates generally to dental implant systems. More particularly, the present invention relates to components used for making a surgical guide that allows for placement of dental implants.

BACKGROUND OF THE INVENTION

The dental restoration of a partially or wholly edentulous patient with artificial dentition is typically done in two stages. In the first stage, an incision is made through the gingiva to expose the underlying bone. After a series of drill bits creates an osteotomy in the bone, a dental implant is placed in the jawbone for integration. The dental implant generally includes a threaded bore to receive a retaining screw holding mating components therein. During the first stage, the gum tissue overlying the implant is sutured and heals as the osseointegration process continues.

Once the osseointegration process is complete, the second stage is initiated. Here, the gum tissue is re-opened to expose the end of the dental implant. A healing component or healing abutment is fastened to the exposed end of the dental implant to allow the gum tissue to heal therearound. Preferably, the gum tissue heals such that the aperture that remains generally approximates the size and contour of the aperture that existed around the natural tooth that is being replaced. To accomplish this, the healing abutment attached to the exposed end of the dental implant has the same general contour as the gingival portion of the natural tooth being replaced.

During the typical second stage of dental restoration, the healing abutment is removed and an impression coping is fitted onto the exposed end of the implant. This allows an impression of the specific region of the patient's mouth to be taken so that an artificial tooth is accurately constructed. After these processes, a dental laboratory creates a prosthesis to be permanently secured to the dental implant from the impression that was made.

In addition to the more traditional system for placing dental implants described above, some systems use guided placement of the dental implants. To do so, a surgical guide is placed in the patient's mouth at the known location. The surgical guide includes openings for providing the exact placement of the drill bits used to create the osteotomy. Once the osteotomy is completed, the surgical guide may permit the dental implant to be placed through the same opening and enter the osteotomy that was guided by the surgical guide.

Surgical guides can be created by the use of a CT-scan of the patient's mouth. The CT-scan provides enough detail to develop the surgical guide by use of various methods. For example, a CT-scan can provide the details of the patient's gum tissue and/or remaining teeth so that the surgical guide can be developed based on computer-aided design (CAD) and computer-aided manufacturing (CAM). One example of the use of a CT-scan is disclosed in U.S. Patent Publication No. 2006/0093988, which is herein incorporated by reference in its entirety. This publication also describes the use of a various tubes that can be placed within the surgical guide to receive the drill bits and implants.

However, a need exists to develop an improved kit of components that can be incorporated in the surgical guide and that can be used in conjunction with the surgical guide. The improved set of components can be used to install the implant such that its non-rotation feature (e.g., hexagonal boss or socket) is at correct orientation when finally installed in the patient's bone via the surgical guide. Furthermore, corresponding laboratory components that are used with the kit would be required as well to develop a temporary or final prosthesis.

SUMMARY OF THE INVENTION

In one aspect, the present invention is a surgical guide for guiding the insertion of a dental implant into a desired location in a patient's mouth. The implant includes a non-rotational structure. The surgical guide includes a structure and a master tube. The structure has a negative impression surface to be fitted on and placed over tissue in the patient's mouth. The structure includes an opening through which the dental implant is placed. The master tube is located at the opening. The master tube includes indicia for alignment with the non-rotational structure on the implant such that the non-rotational structure of the implant is at a known angular orientation with respect to the master tube. The structure could be made from one of many materials, such as polymeric materials used to create the structure via rapid prototyping. The tissue on which the surgical guide is fitted can be the bone, adjacent teeth, and/or soft tissue.

According to a further aspect of the invention, a method of installing a dental implant in a patient's mouth comprises (i) placing a surgical guide over the gum tissue in the patient's mouth wherein the surgical guide includes an opening for receiving the dental implant, (ii) inserting the implant into the opening by applying rotational force to the implant; and (iii) stopping the insertion in response to a non-rotational feature on the implant or (an implant mount attached the implant) being aligned with indicia along the opening such that the non-rotational feature is at a known position with respect to the opening.

In another aspect, the present invention is a method of manufacturing a dental prosthesis for placement in a patient's mouth, comprising (i) determining the location of at least one dental implant to be placed in the mouth of the patient, (ii) developing a surgical guide to be used in the placement of the at least one dental implant in the patient's mouth, wherein the surgical guide fits over the gingival tissue and includes an opening and a marker adjacent to the opening for indicating the alignment of a non-rotational feature of the at least one dental implant, (iii) developing a stone model of the patient's mouth using the surgical guide, (iv) developing the dental prosthesis on the stone model, wherein the dental prosthesis includes a mating structure for mating with the non-rotational feature of the at least one dental implant, (v) placing the surgical guide in the patient's mouth, (vi) installing the at least one dental implant through an opening in the surgical guide such that the non-rotational feature is aligned with the marker, (vii) after installing the implant, removing the surgical guide from the patient's mouth; and (viii) attaching the dental prosthesis to the at least one dental implant.

In a further aspect, the present invention involves a kit of components for guiding the insertion of a dental implant into a desired location in a patient's mouth. The implant including a non-rotational structure. The kit includes a surgical guide and a plurality of guide tubes. The surgical guide has a negative impression surface to be fitted on and placed over at least a portion of the gingival tissue in the patient's mouth. The surgical guide includes at least one master tube defining an opening through which the dental implant is placed. The master tube includes a marking to provide alignment with the non-rotational structure on the dental implant. Each of the guide tubes has an outer surface for mating with the master tube and an inner surface for engaging a drill bit for developing an osteotomy into which the implant is received. The guide tubes may include handles.

In an alternative aspect, the present invention is kit of components for developing a stone model of a patient's mouth. The stone model includes implant analogs that replicate dental implants. The kit comprises a surgical guide and a plurality of implant analog-mounts. The surgical guide has a negative impression surface of at least a portion of the gingival tissue in the patient's mouth. The negative impression surface includes at least one master tube defining an opening through which the implant analogs are placed. The plurality of implant-analog mounts are for attachment to the implant analog. Each of the implant-analog mounts are insertable into the master tube and include an expandable region that locks the implant-analog mount into the master tube for maintaining the position of an attached implant analog relative to the surgical guide.

In yet another aspect, the invention is an implant-analog mount comprising a main body and an expandable region. The main body has a lower portion for attachment to an implant analog. The expandable region is at the upper portion of the main body. The expandable region locks the implant-analog mount into a surrounding structure that is used for creating a stone model of the patient's mouth.

In a further aspect, the present invention is a master tube for use in a surgical guide for guiding the insertion of a dental implant in a patient's mouth. The master tube comprises a main body and indicia. The main body has an opening therethrough. The indicia is for alignment of a non-rotational structure on the implant at a known angular orientation with respect to the master tube.

BRIEF DESCRIPTION OF THE DRAWINGS

FIG. 1b schematically illustrates the various axially oriented dimensions of the components in FIG. 1a;

FIG. 2b is an isometric view of the implant mount of FIG. 2a;

FIG. 6b is a side view of the master tube of FIG. 6a;

FIG. 7b is a top view of the implant-analog mount of FIG. 7a;

Figure 1A:
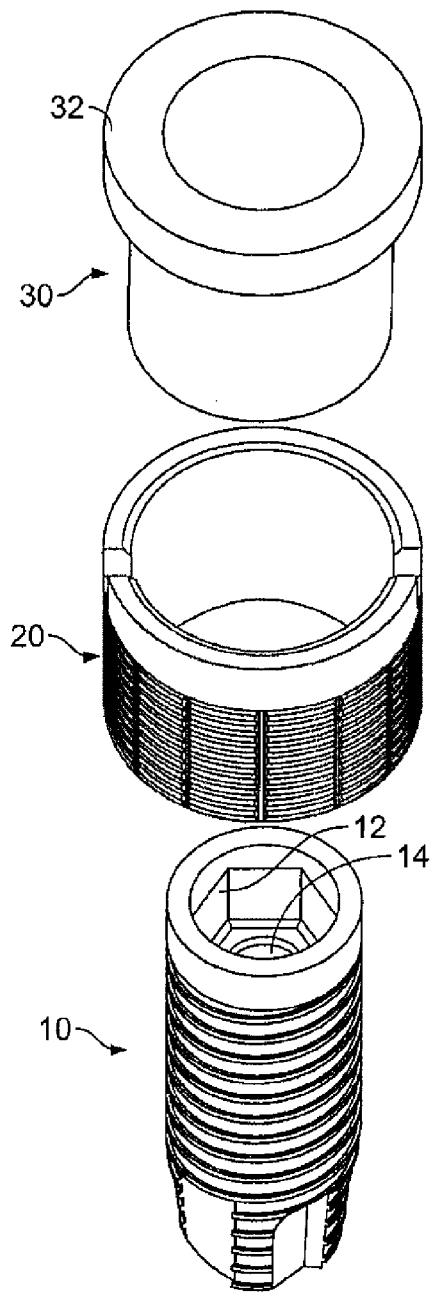
FIG. 1a illustrates an implant, a master tube for use in a surgical guide, and a guide tube for use with the master tube.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

DESCRIPTION OF ILLUSTRATIVE EMBODIMENTS

Figure 1B:
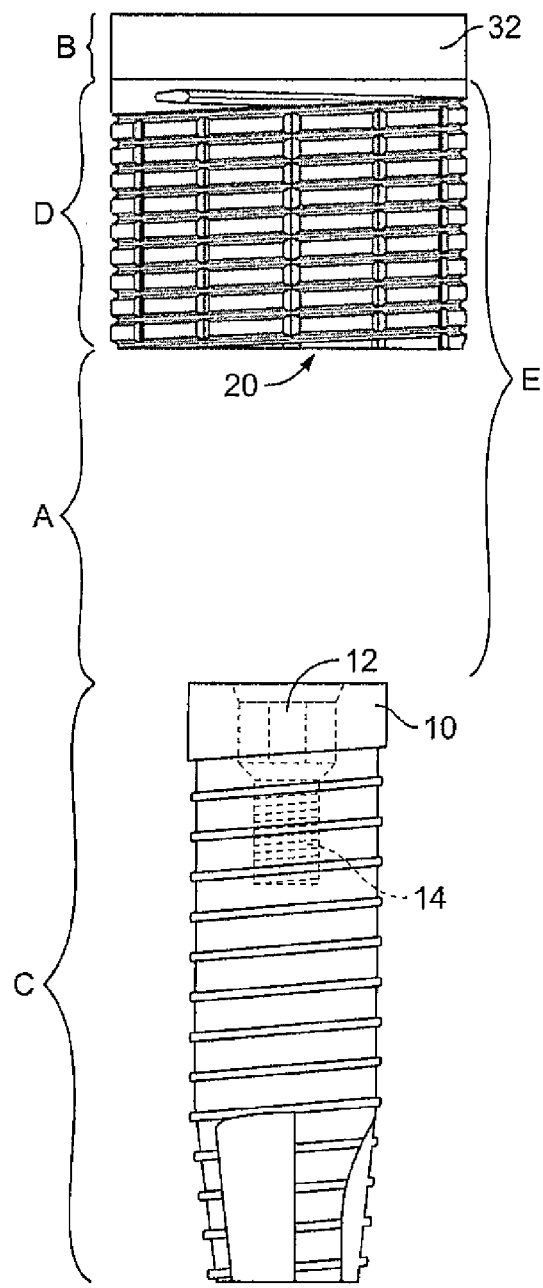

FIG. 1A illustrates some of the external components used for installing a dental implant 10 during dental surgery in the patient's mouth in accordance with a predetermined dental plan. FIG. 1B illustrates the dimensions, which are discussed in more detail below, that are used to ensure the proper axial location of the dental implant 10 in the patient's bone. As shown, the implant 10 includes a non-rotational feature 12 in the form of a hexagonal socket and a threaded bore 14 located below the non-rotational feature 12. The non-rotational feature 12 can also be in other internal forms, such as a different polygonal or non-round shapes, and it can also be present in an external form, such as in a hexagonal boss that protrudes above the top surface of the implant 10. The external components include a master tube 20 that will be located within a surgical guide, which is discussed in more detail below, and a guide tube 30 have an upper lip 32. The guide tube 30 is like a bushing that fits snugly within the master tube 30 such that the upper lip 32 rests on the upper surface of the master tube 20.

A dental plan for the patient may be developed by scanning the patient's mouth with a CT scanner (or other scanning technologies or devices) to obtain the details of the bone structure, teeth and overlying gingival tissue. When considering the dental plan for a specific patient, especially one that involves the placement of several dental implants, the location of the implant(s) 10 relative to the surface of the gingival tissue and underlying bone is important. Additionally, the maximum depth of the distal end of the implant 10 within the bone is also important, so as to avoid the sinus cavity and mandibular canal. To ensure the proper location for each implant 10 (and the osteotomy for each implant 10), the scanning of the patient's mouth can be used to develop a surgical guide (e.g., by rapid prototyping) that fits snugly onto the surface of the tissue by having a negative impression that incorporates the details of the tissue surface in the patient's mouth. By the term "tissue" in the present specification, it is understood that tissue can be hard tissue (such as bone tissue or teeth) and soft tissue (such as the gingival tissue). The remainder of the detailed description will assume that the patient is edentulous and that the surgical guide is resting on the soft tissue.

With reference to FIG. 1B, to properly locate the implant 10 in the axial direction in accordance with the dental plan, the length dimension "C" of the implant 10 must be known. Further, the dimension "A" is the distance from the seating surface of the implant 10 to the bottom of the master tube 20, which has a known length of dimension "D." Dimension "B" is the thickness of the lip 32 of the guide tube 30, which receives the drill bits for drilling the osteotomy. Dimension "E" is the length dimension of an implant mount 40 (FIG. 2; and implant-analog mount 100 of FIG. 7)) that will be attached to the implant 10 and used to drive the implant 10 into the bone in accordance to the dental plan. The surgical guide, discussed below, will have an axial dimension directly over each implant 10 that is greater than dimension "D," but less than dimension "E." This axial dimension of the surgical guide over the dental implant 10 will be chosen to ensure that the distance "E" is equal to one of several known and standard lengths for the implant mount 40 (e.g., 7.5 mm, 9 mm, 10.5 mm, 12 mm). In short, once the scan of the patient's mouth is known, the dimensions "A", "B", "C", "D", and "E" of FIG. 1B are also considered to develop a surgical guide that will place each dental implant 10 in accordance to the dental plan.

Figure 2A:
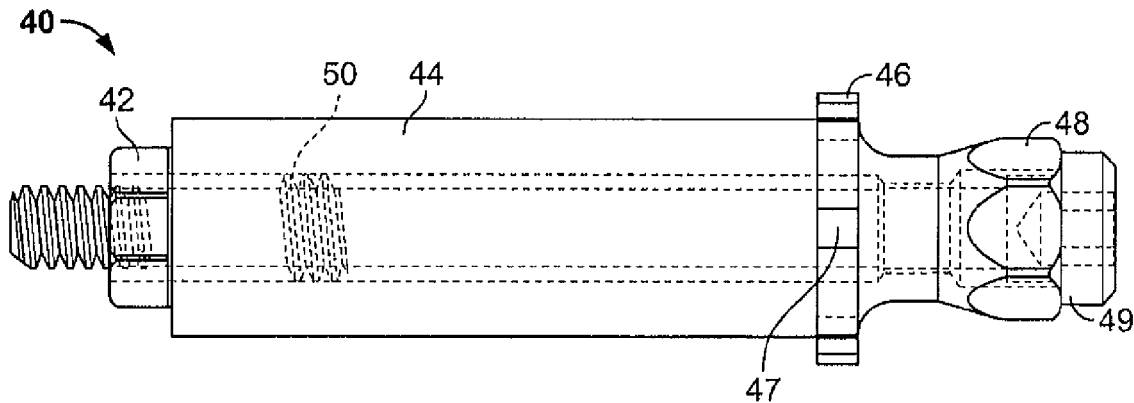
FIG. 2a is a side view of an implant mount for use in driving an implant into the osteotomy in the patient's mouth.
Figure 2B:
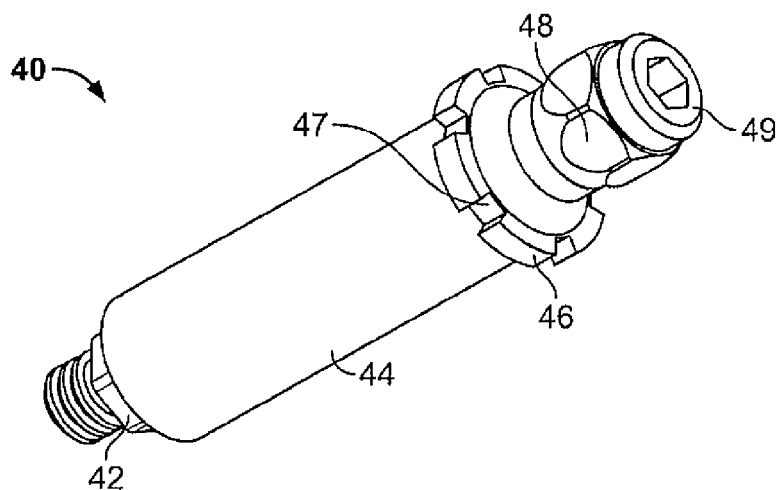
Figure 2C:
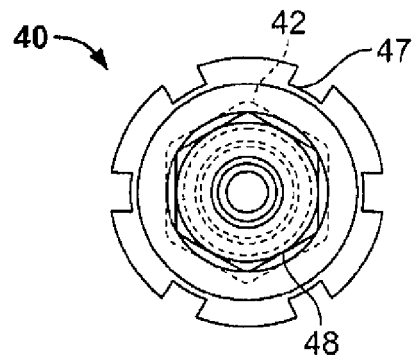
FIG. 2c is a top view of the implant mount of FIGS. 2a and 2b.

FIGS. 2A, 2B, and 2C illustrate one length of the implant mount 40 that is used with the dental implant 10. As will be discussed with reference to FIG. 12, the implant mounts 40 are available in several lengths and diameters for different implant widths. The implant mount 40 includes a non-rotational feature 42 (as shown, a hexagonal boss) at one end of a main body 44 for mating with the non-rotational feature 12 of the implant 10. At the other end of the main body 44 is a flange 46 having a plurality of notches 47. A driving element 48 is located above the flange 46 for receiving torque from a manual or power drive to rotate the attached implant 10 into the bone of the patient. The implant mount 40 further includes a bore that receives a screw 49 extending through the entire implant mount 40. The bore may include internal threads 50 for capturing the threads of the screw 49 such that the screw 49 and the implant mount 40 are held together even when the implant mount 40 is unattached to a dental implant 10.

For visual alignment purposes, each notch 47 is aligned with one surface of the non-rotation feature 42 of the implant mount 40. In the illustrated embodiment, each notch 47 is also aligned with one surface of the driving element 48. Thus, the notches 47 help to identify the orientation of the underlying non-rotational feature 42. This is important because, once the implant 10 is installed in the patient's bone, the non-rotational feature 12 of the implant 10 must be at a known angular position in the patient's bone for a predefined prosthetic component (e.g., a bar, an abutment, etc) to be aligned in the proper angular orientation when its non-rotational feature mates with the non-rotational feature 12 of the implant 10.

Figure 3:
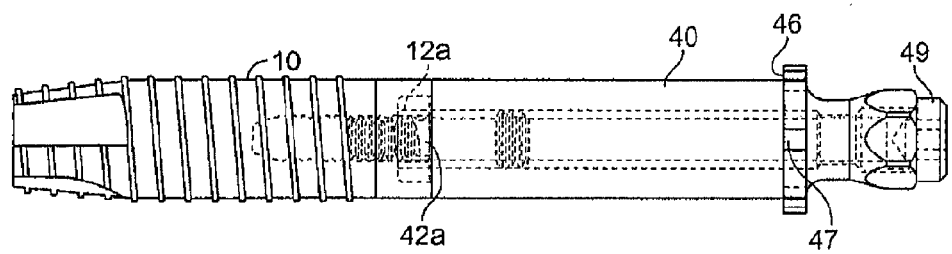
FIG. 3 illustrates the implant mount of FIG. 2 attached to the implant of FIG. 1.

FIG. 3 illustrates the dental implant 10 attached to the implant mount 40 via the screw 49. Additionally, the non-rotational feature 12 of the implant 10 is coupled to the non-rotational feature 42 of the implant mount 40. Due to the position of the notches 47 on the flange 46, each notch 47 is aligned with corresponding surfaces 12a, 42a of the non-rotational features 12, 42. Accordingly, although the clinician cannot see the non-rotational feature 12 of the implant 10, the clinician still knows the angular orientation of the non-rotational feature 12 by inspection of the notches 47 on the implant mount 40.

Figure 4:
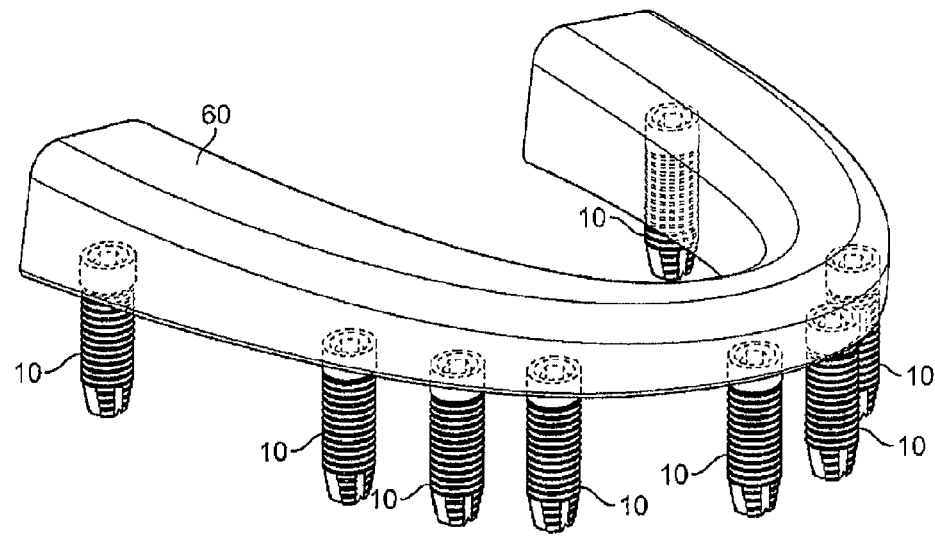
FIG. 4 is an illustration of the virtual installation of eight dental implants under the gingival surface overlying the mandible in the patient's mouth.

FIG. 4 schematically illustrates a computerized dental plan that is created by scanning the patient's mouth. The scan reveals a virtual gingival surface 60 that would overlay the bone structure in the patient's mouth. To provide structural support for a bar-type denture for a prosthesis, the dental plan in FIG. 4 includes eight dental implants 10 (virtual implants in FIG. 4) placed at specific locations and angles in the patient's bone. The sizes of the dental implants 10, as well as their locations and angles, are chosen based on the various bone densities and underlying tissue (e.g., sinus cavity or mandibular canal) provided by the scan or other means. These adjustments are preferably made through inputs to a computer to define the best possible dental plan for the particular patient. In the illustrated embodiment, the gingival surface 60 represents the gingiva overlaying the maxilla, such that the dental implants 10 extend upwardly toward the sinus cavity. As described in the sequence of steps listed below, the end result of the dental plan is that eight dental implants 10 are installed in the patient's maxilla at the depths and angles defined by the dental plan, and the eight dental implants 10 are then attached to a bar structure that is part of the denture-type dental prosthesis that is developed for that particular patient.

Figure 5:
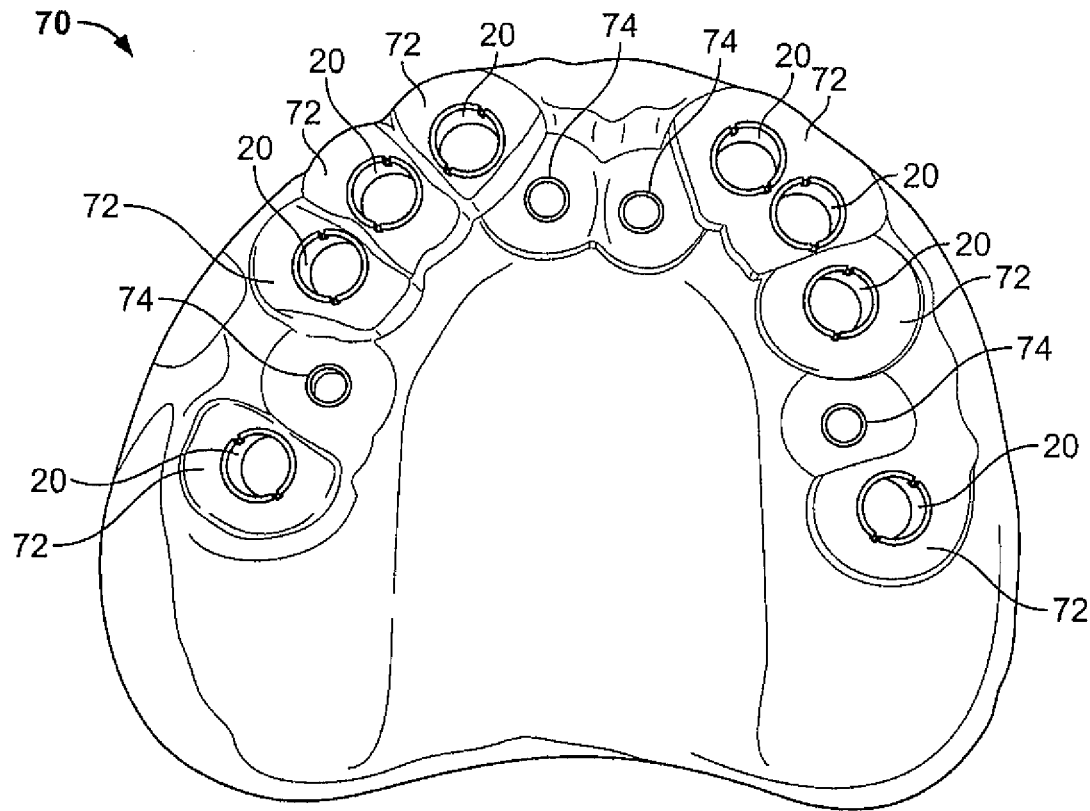
FIG. 5 is a top view of a surgical guide that is used in the patient's mouth to guide the placement of the eight implants in accordance to the planned installation of FIG. 4.

Based on the dental plan of FIG. 4, a surgical guide 70 is developed, as shown in FIG. 5. The surgical guide 70 can be produced from various materials and techniques. One preferred method is using a rapid-prototyping technique based on the scanned images within the patient's mouth. Because there is a need for eight implants 10, the surgical guide 70 includes eight openings, each of which is defined by a master tube 20 that is integrated into the material of the surgical guide 70 with the assistance of the outer roughened surface and adhesive. The master tubes 20 are located on flat surfaces 72 that are substantially flush with the top surface of the master tubes 20. The under portion of the surgical guide 70 (not visible in FIG. 5) has a contour that follows the scanned gingival surface 60 (FIG. 4) in the patient's mouth. In other words, the under portion of the surgical guide 70 is a negative impression of the gingival surface 60. The surgical guide 70 also includes a plurality of openings 74 through which temporary fixation screws or pins can be placed. The temporary fixation screws or pins engage the bone and hold the surgical guide 70 in the proper location on the gingival surface 60 (FIG. 4) so that the dental plan can be executed using the surgical guide 70. As mentioned previously, the surgical guide 70 can also be a negative impression of the surface of adjacent teeth and bone tissue in some situations and rest against the adjacent teeth and bone tissue.

As indicated previously, the implant mounts 40 of FIG. 2 are available in different sizes. Thus, depending on the contours of the gingival tissue 60, each flat surface 72 can be raised or lowered during its design to ensure the proper distance for dimension "E" in FIG. 1B, when considering the length of the implant mount 40 that was chosen.

Figure 6A:
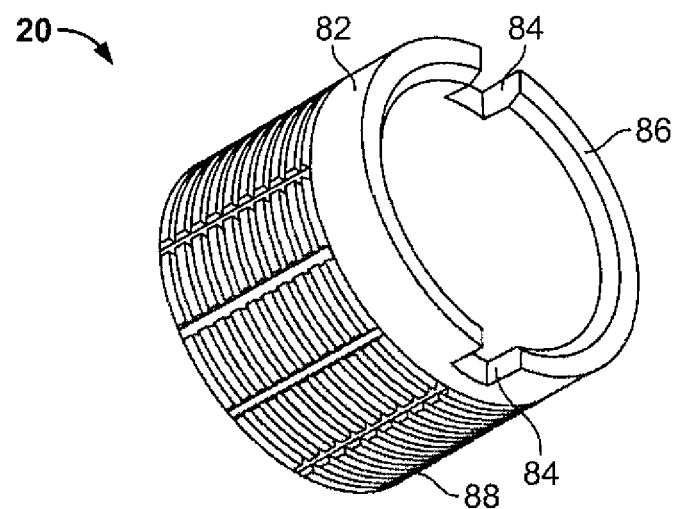
FIG. 6a is an isometric view of a master tube that is placed in the surgical guide of FIG. 5.
Figure 6B:
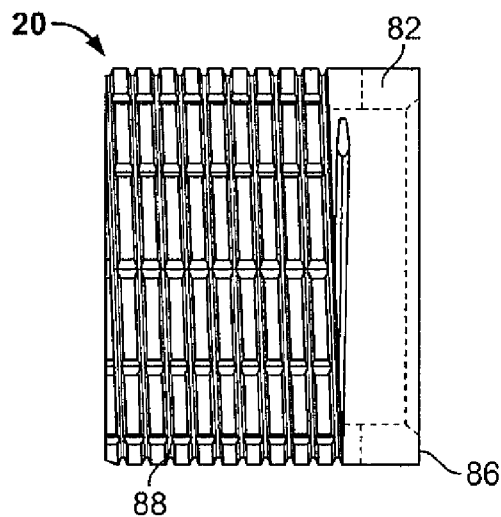
Figure 6C:
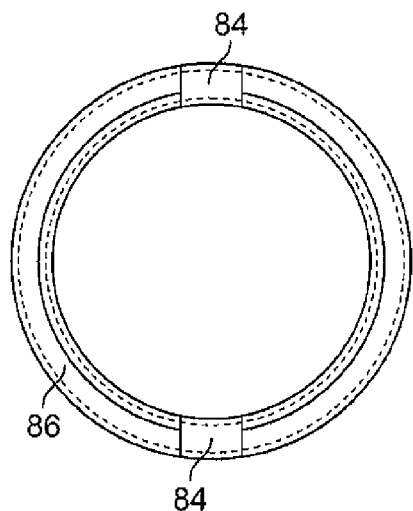
FIG. 6c is a top view of the master tube of FIGS. 6a and 6b.

FIGS. 6A-6C illustrate the details of the master tube 20. The master tube 20 includes a main body 82 with notches 84 located on the upper surface 86. The master tube 20 includes a roughened side surface 88 that allows the master tube 20 to be better attached to the material of the surgical guide 70. As shown, the roughened surface 88 includes a spiral groove around the circumference of the main body 82 and axial grooves along the central axis of the main body 82 that intersect the spiral grooves. In other embodiments, the main body 82 can be a knurled surface, or have any other surface structure allowing it to be fixed within the material of the surgical guide 70.

The master tube 20 may come in different sizes to accommodate dental implants having different diameters. For example, a master tube 20 with an internal 4.1 mm diameter may be used for implants 10 having diameters of 4.0 mm or smaller. And, a master tube 20 with an internal 5.1 mm diameter may be used for implants 10 having diameters of between 4.0 mm and 5.0 mm.

Figure 7A:
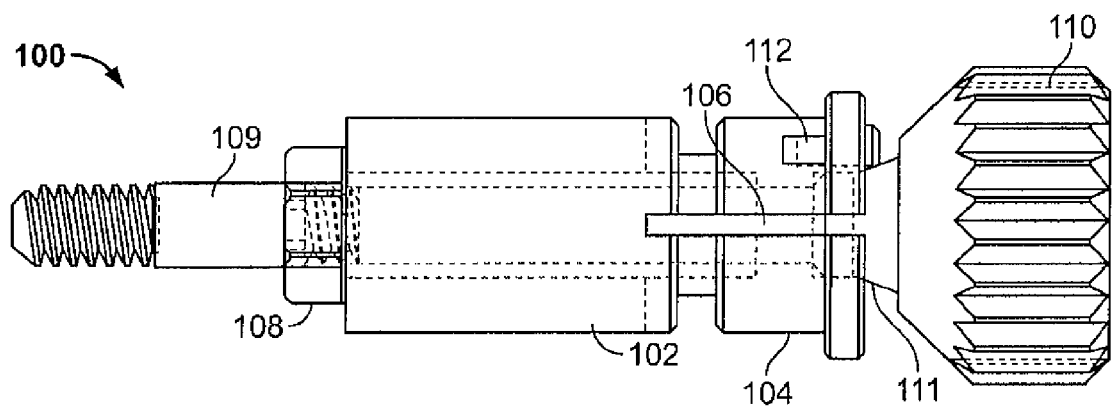
FIG. 7a is a side view of an implant-analog mount that is used in conjunction with the surgical guide of FIG. 5 to develop a model of the patient's mouth.
Figure 7B:
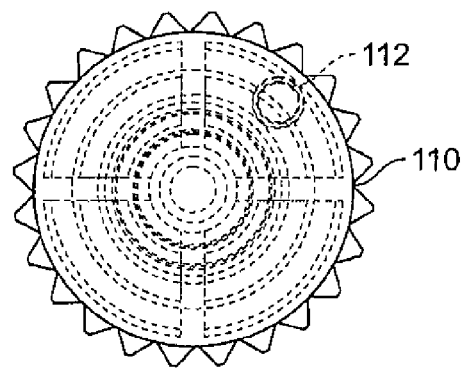

In some situations, the surgical guide 70 can be used to develop a stone model of the patient's gingival surface 60 since its underlying surface is a negative impression of the patient's gingival surface 60. When this occurs, the surgical guide 70 performs two different functions—development of the stone model representing the prevailing conditions in the patient's mouth and surgical placement of the implants 10 in the patient's mouth. FIGS. 7A and 7B illustrate an implant-analog mount 100 that, in conjunction with the surgical guide 70, can be used for developing a model of the gingival surface 60 of the patient's mouth. The implant-analog mount 100 includes a main body 102 and an expandable top section 104, which includes a plurality of slots 106. The lower end of the main body 102 includes a non-rotational feature 108 (here, a hexagonal boss) that will engage a corresponding mating surface in the implant analog. The implant-analog mount 100 includes a screw 109 with a large rotatable head 110. When the rotatable head 110 is tightened, such that the screw 109 is tightened into the implant analog, then further rotation causes the tapered section 111 of the screw 109 to force the expandable top section 104 outwardly.

An orientation marker 112 is located on the expandable top section 104 and is aligned with one of the flat surfaces on the non-rotational feature 108. The orientation marker 112 extends below the top flange of the expandable top section 104 and, as described below, mates with the notch 84 within the master tube 20 when developing the stone model.

Figure 8:
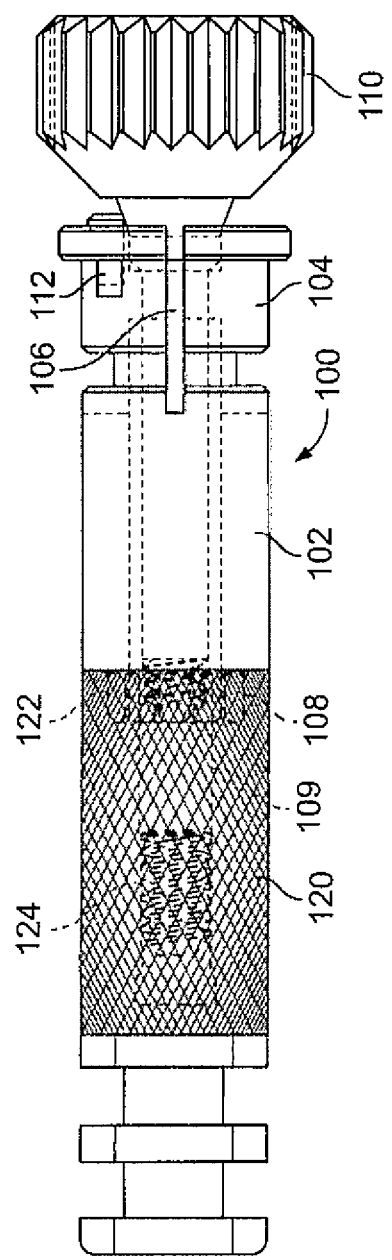
FIG. 8 is a side view of the implant-analog mount in FIG. 7 that is used with an implant analog.

FIG. 8 illustrates the implant-analog mount 100 attached to an implant analog 120, which will be encased in a stone model. The implant analog 120 has an upper surface that replicates the upper surface of the dental implant 10 and serves the purpose of allowing a dental prosthesis to be built on the stone model so that the prosthesis can be later transferred to the patient's mouth and be attached to the dental implant 10 in a similar manner. Thus, the implant analog 120 includes a non-rotation feature 122 that mates with the non-rotational feature 108 of the implant-analog mount 100. When doing so, the orientation marker 112 is then aligned with the non-rotation feature 122 of the implant analog 120. The implant analog 120 also includes internal threads 124 for receiving the screw 109 to hold the implant analog 120 to the implant-analog mount 100.

Figure 9A:
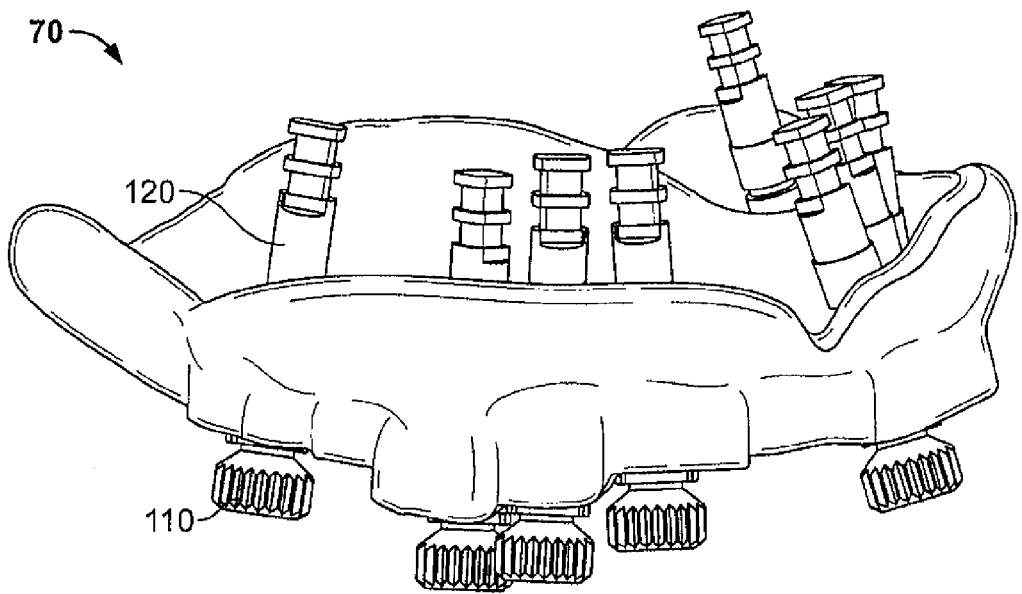
FIG. 9A illustrates the combination of the implant-analogs and associated mounts of FIG. 8 after being placed in the surgical guide.
Figure 9B:
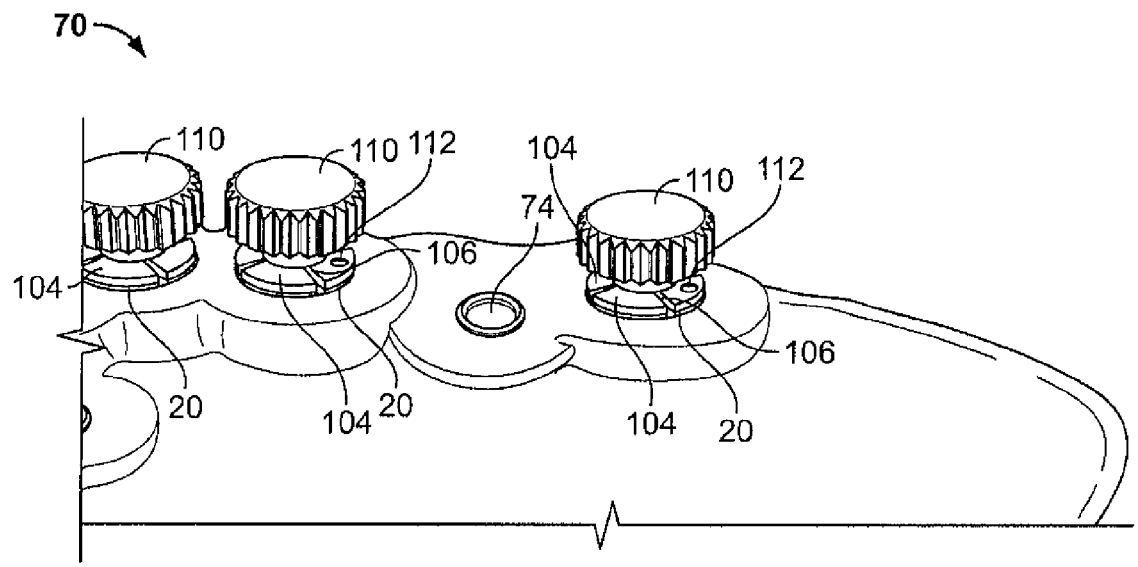
FIG. 9B also illustrates the combination of the implant-analogs and associated mounts of FIG. 8 after being placed in the surgical guide.

FIGS. 9A and 9B illustrate the implant-analog mounts 100 and implant analogs 120 located within the eight openings of the surgical guide 70. As shown best in FIG. 9B, the top flange of the expandable top section 104 rests on the master tube 20 with the orientation marker 112 fitting within one of the two notches 84 of the master tube 20. As such, the location of the non-rotational feature 122 of the implant analog 120 is known and fixed relative to the surgical guide 70. Once properly seated, the large rotatable head 110 is rotated a bit more (typically less than ½ revolution) to cause the expandable top section 104 to expand outwardly into the master tube 20 and lock itself into axial position.

Figure 10A:
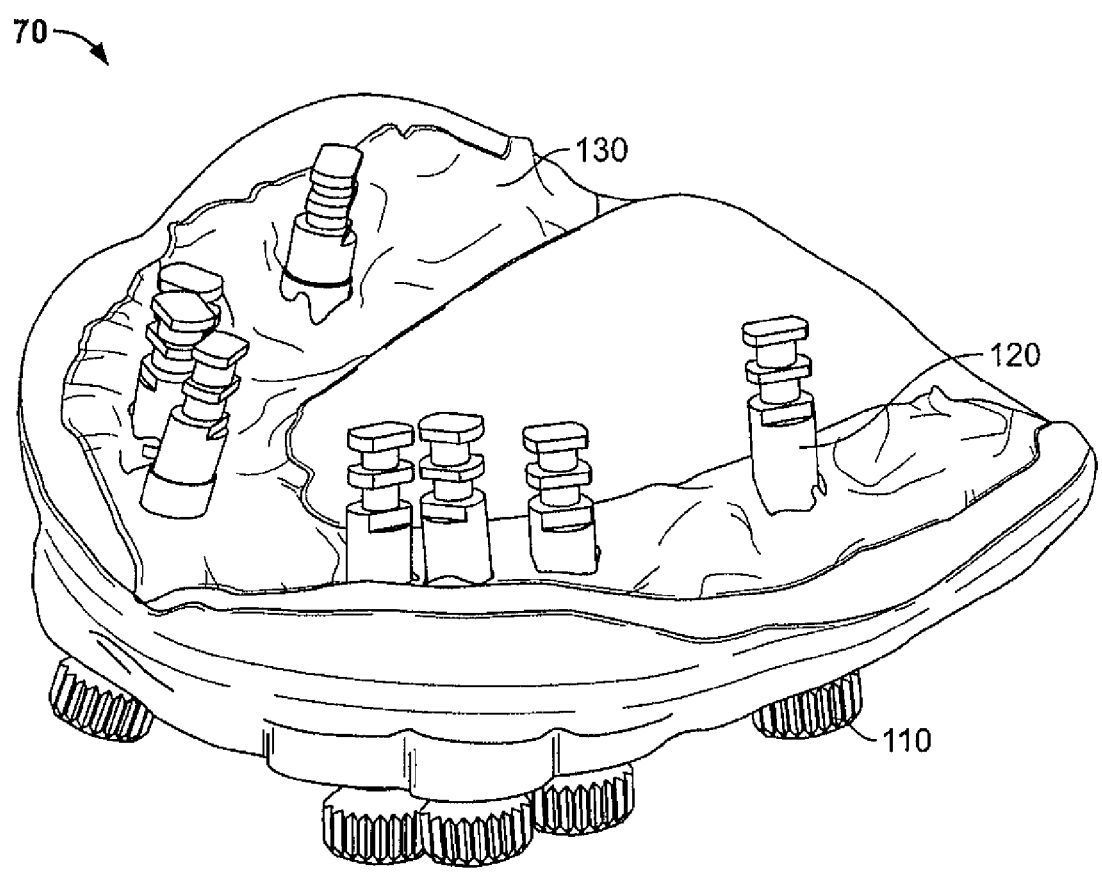
FIG. 10A illustrates impression material being used with the combination of components in FIG. 9 to develop a stone model of the patient's mandible.

FIG. 10A illustrates the making of a model with the surgical guide 70. In one preferred embodiment, the model preferably includes a soft-tissue model aspect that is located over the stone model. In the illustration of FIG. 10A, the flowable material 130 enters the surgical guide 70, which has a contour that is the negative impression of the gingival surface that was scanned to develop the virtual gingival surface 60 in FIG. 4. The flowable material 130 is preferably about 2 mm in depth, which generally matches the thickness of the gingiva. When hardened, the flowable material 130 is resilient so as to replicate the soft tissue. Then, stone is poured onto the backside of the flowable material 130 to encase the implant analogs 120. Because of the orientation marker 112 and the locking of the expandable top section 104, the implant analogs 120 do not move when acted upon by the flowable material 130. Once all of the flowable material 130 and stone has hardened, the large rotatable head 110 is loosened, which unlocks the implant analog mount 100 from the master tube 20 and, eventually releases the implant analog 120, such that implant analog mount 100 can be removed from the surgical guide 70. It should be noted that the skilled artisan will recognize that there are many ways to make a model, using various materials.

Figure 10B:
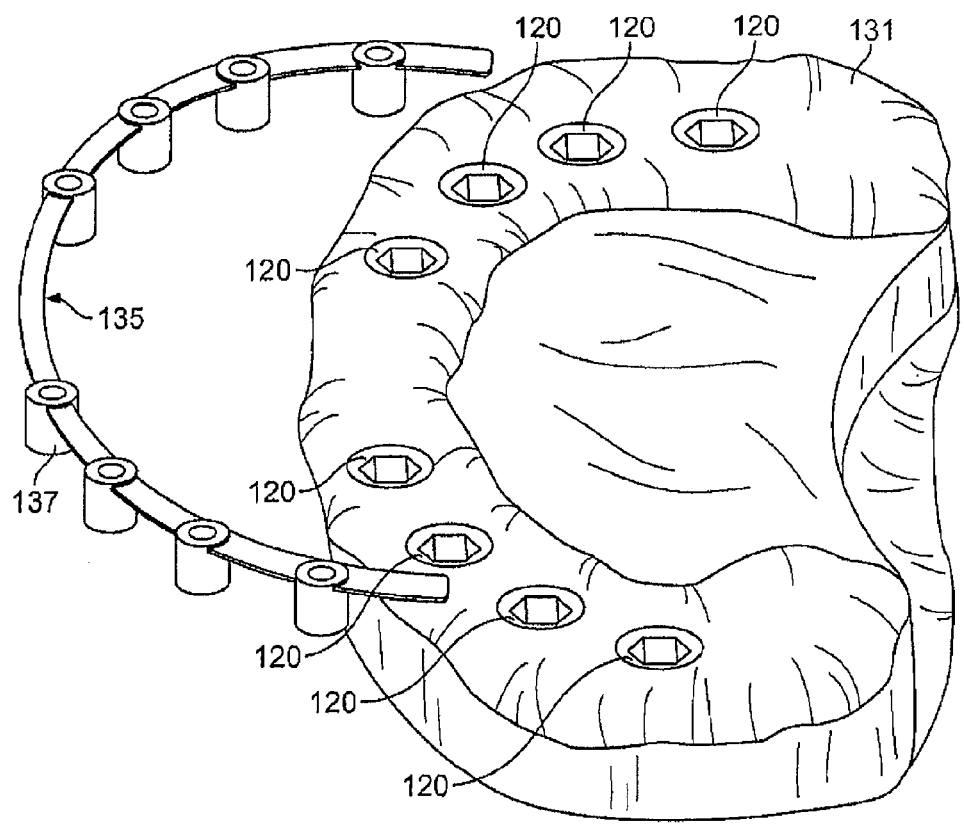
FIG. 10B illustrates the stone model of FIG. 10A, along with a dental bar, which is made using the stone model and which is part of the temporary or final dental prosthesis.

FIG. 10B illustrates the stone model and soft tissue model once it has been removed from the surgical guide 70. These stone and soft tissue model will now be collectively referred to as the model 131. The model 131 includes the eight implants analogs 120 that will replicate the positions of the eight dental implants 10 that will be inserted into the patient's bone by use of the surgical guide 70. As such, a temporary or permanent prosthesis can be built using the model 131, along with the use of other common devices and tools, such as an articulator. As shown in FIG. 10B, the prosthesis includes a dental bar 135 that can receive a denture that clips onto the bar 135. The dental bar 135 would include attachment regions 137 for mating with the implant analogs 120 in the model 131 using a screw. Eventually, the dental bar 135 will mate with the eight dental implants 10 to be installed in the patient's mouth using the same surgical guide 70 (or a second surgical guide similarly structured).

Figure 11:
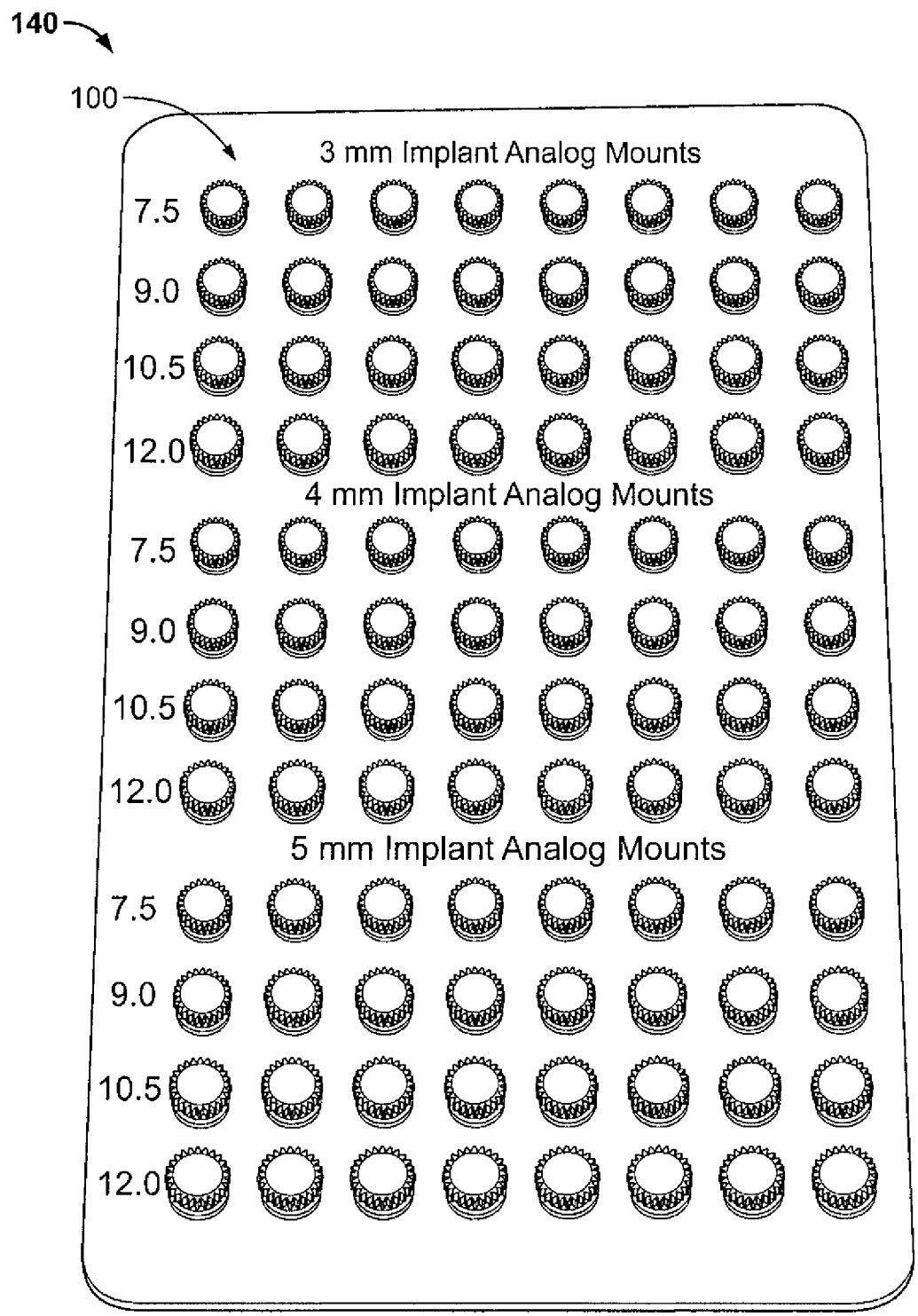
FIG. 11 illustrates a kit, or a portion of kit, containing various sizes of implant-analog mounts that are used for developing the model, as set forth in FIGS. 9-10.

FIG. 11 illustrates a kit 140, or a portion of a larger kit, that includes various sizes of the implant-analog mounts 100. Because the dental plan can require different depths for the implants 10 and, thus, different sizes for the implant analogs 40, the implant-analog mounts 100 must be available in various lengths and diameters. Further, the implant-analog mounts 100 must be able to accommodate various diameters of implant analogs 40, which correspond to various diameters of dental implants 10. As shown, for each of the 3 mm, 4 mm, and 5 mm diameters of the implant-analog mounts 100, the available lengths are 7.5 mm, 9.0 mm, 10.5 mm, and 12.0 mm. As shown, there is eight implant-analog mounts 100 for each size because a dental plan may require multiple uses of the same size (e.g., eight implants 10 in the dental plan in the illustrative embodiment).

Figure 12:
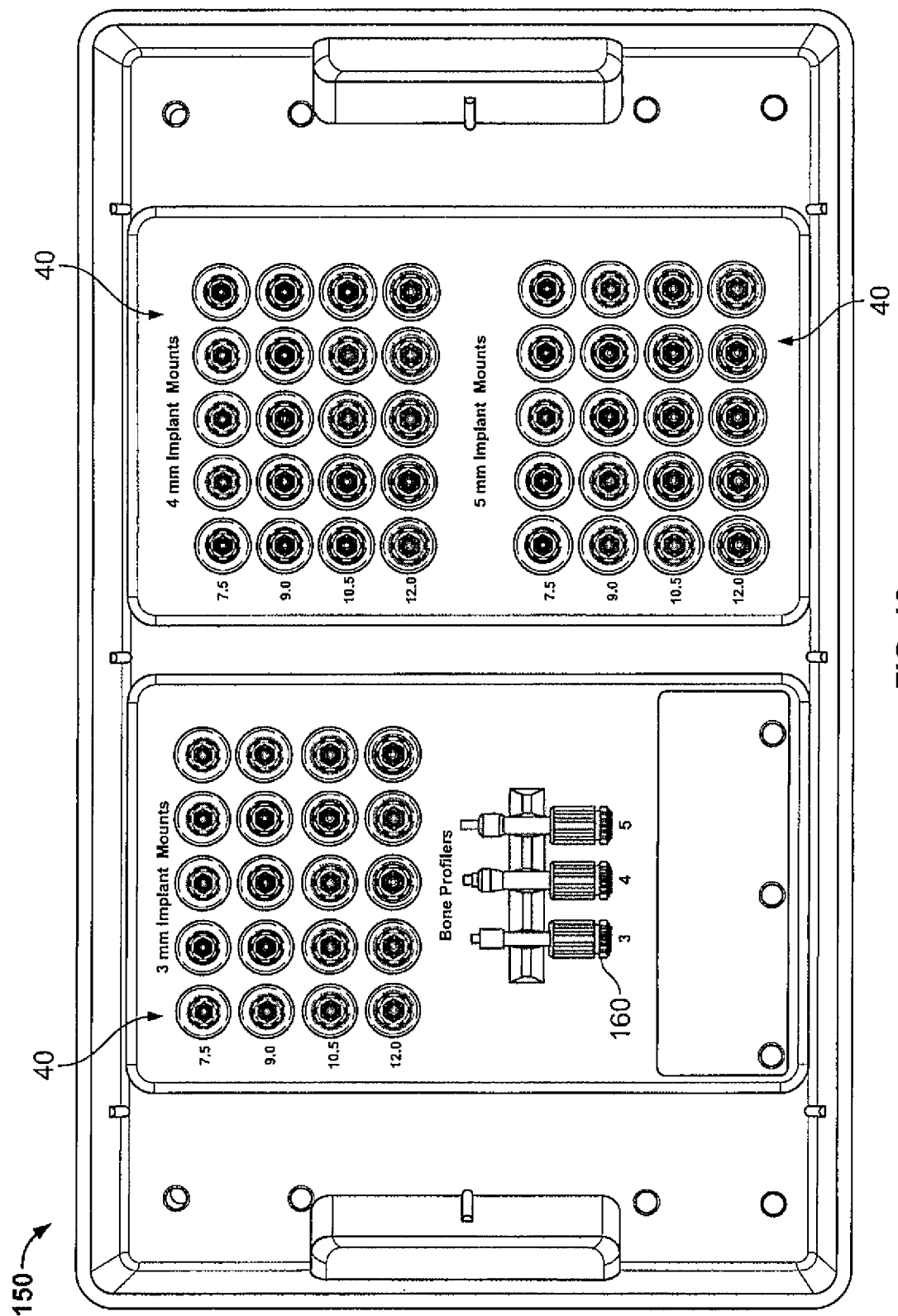
FIG. 12 illustrates a kit, or a portion of a kit, containing various sizes of the implant mount as set forth in FIGS. 2 and 3.

Similarly, FIG. 12 illustrates a kit 150, or a portion of a larger kit, which includes various sizes of the implant mounts 40. For each of the 3 mm, 4 mm, and 5 mm diameters of the implant mounts 40 for mating with correspondingly sized implants 10, the available lengths are 7.5 mm, 9.0 mm, 10.5 mm, and 12.0 mm. Again, the dental plan may require a set of implants 10 having different lengths and that are positioned in at different depths in the bone. Thus, the various lengths of the implant mounts 40 are needed to accommodate those dimensional variables when considering the thickness of the surgical guide 70 and dimension "E" of FIG. 1B. Likewise, the implant analog mounts 100 of FIG. 11 for constructing the stone model 131 must also be available in different lengths corresponding to the lengths of the implant mounts 40.

FIG. 12 also illustrates an additional set of components, bone profilers 160, which are useful for surgery with the surgical guide 70. The bone profilers 160 are used after drill bits have create the osteotomy and the implants 10 have been installed. After the surgical guide 70 is removed, the bone profiler 160 mates with the top surface of the implant 10, and is rotated to remove any remaining overhanging bone tissue to create easy access to the dental implant 10. Further, the bone profiler 160 creates an emergence profile that is equivalent to the restorative abutment to be used.

Figure 13:
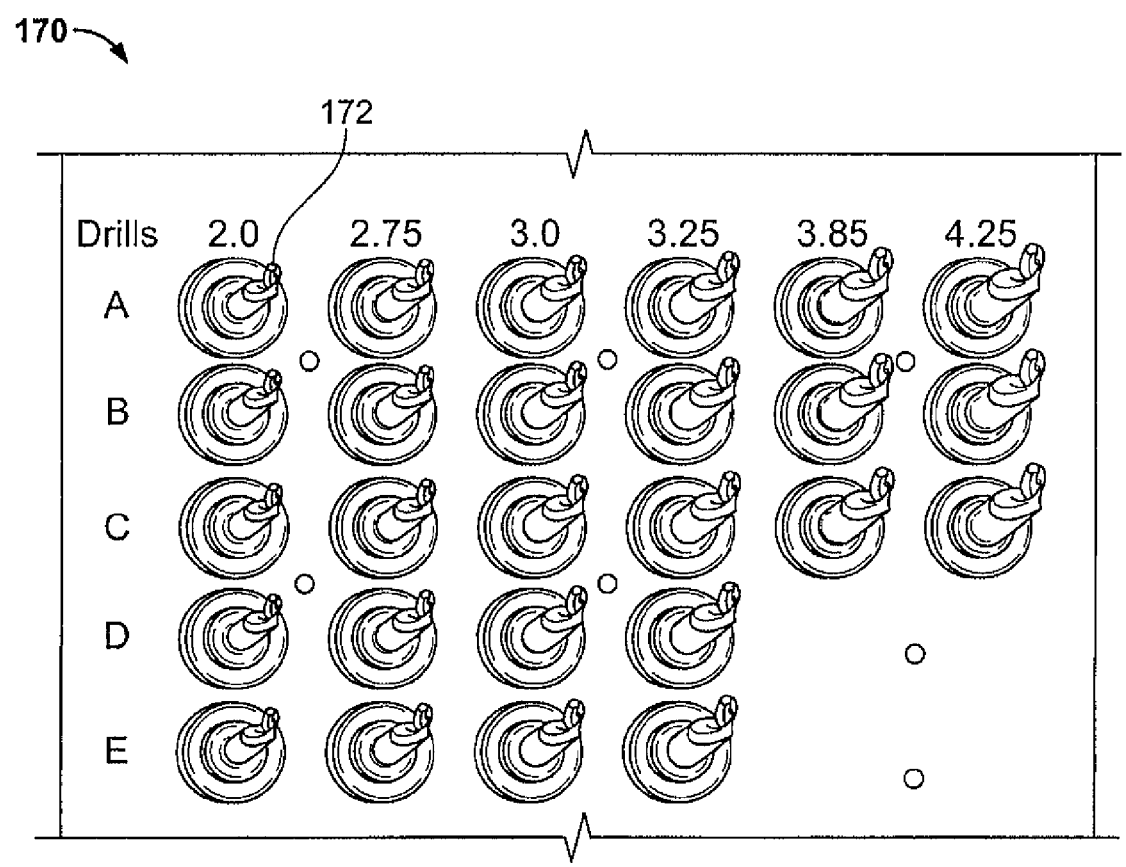
FIG. 13 illustrates a kit, or a portion of a kit, containing various sizes of dental drills that are used with the surgical guide to create an osteotomy in the patient's mouth.

FIG. 13 illustrates a kit 170 of drill bits 172 that are used to create the osteotomy. Each of the drill bits 172 is of a different size in the length dimension (A, B, C, D, and E) and diametric dimension (2.0 mm, 2.75 mm, 3.0 mm, 3.25 mm, 3.85, mm, 4.25 mm). Each drill bit 172 has a stop flange that engages the top surface of the flange 32 of the guide tube 30 (FIG. 1A) to control its depth of insertion. Thus, when the dental plan is established, a specific series of drill bits 172 is chosen to be sequentially used with the surgical guide 70. For example, for a certain dental implant 10 to be installed, the dental plan may call for the drill bits of B-2.0 mm and B-3.25 mm. The dimensions of the osteotomy are defined by the last drill bit 172 (B-3.25 mm), which has a drill bit length dimension that substantially corresponds to the summation of dimensions "B", "D", "A", and "C" in FIG. 1B.

Preferably, the drill bits 172 have cutting flutes at only the lower portion of the shank, such as over the lowermost 2 mm or 3 mm of length. Thus, the drill bits 172 do not cut into and damage the internal surface of the guide tubes 30 as they rotate.

Figure 14:
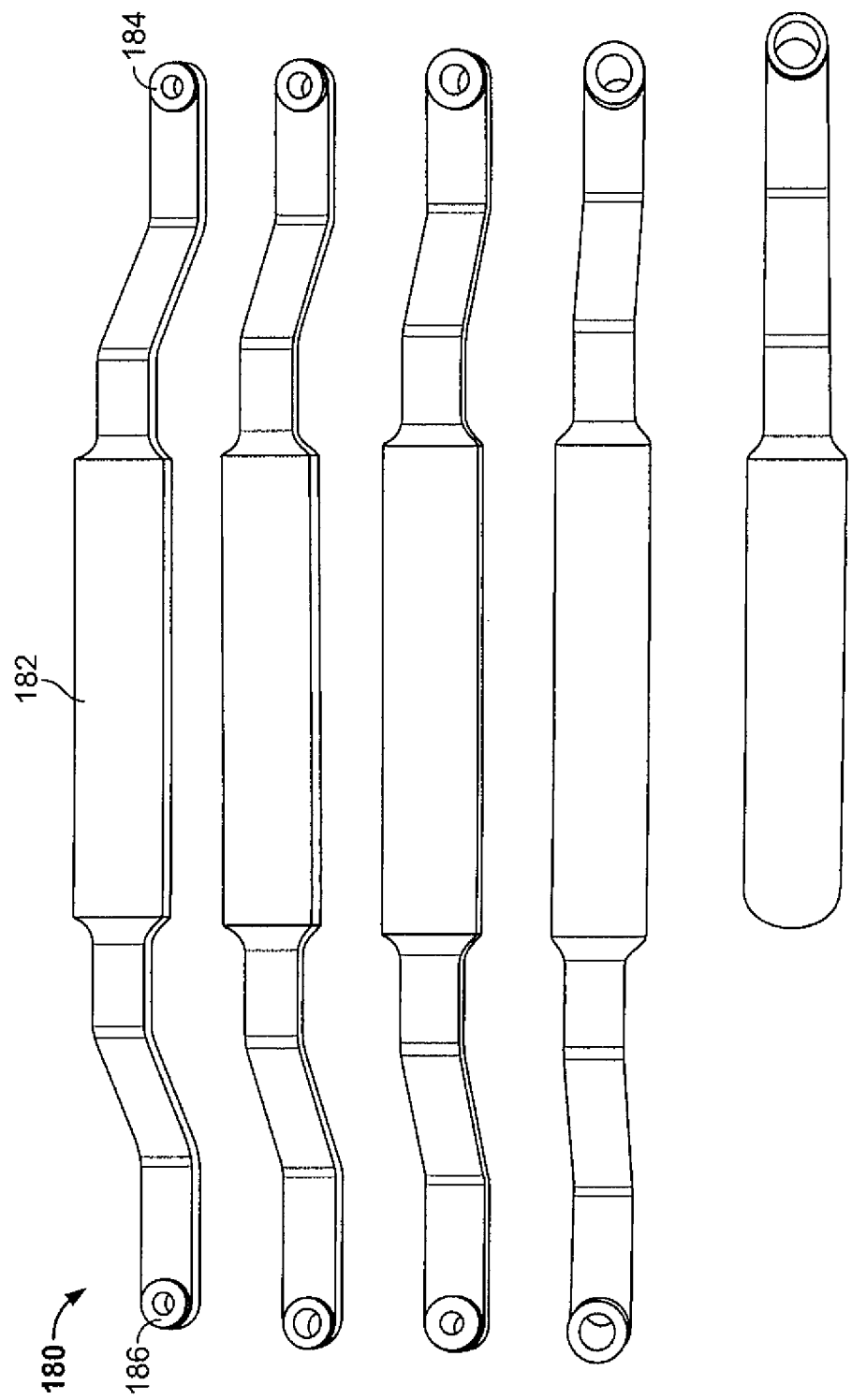
FIG. 14 illustrates a kit of guide-tube tools for use with the surgical guide when the surgical guide is placed in the patient's mouth.

FIG. 14 illustrates a series of guide-tube tools 180. Each of the guide-tube tools 180 include a handle region 182 to be manually grasped. At both ends of the guide-tube tools 180, there are guide tubes 184 and 186, which have a bushing-like structure that is similar to the guide tube 30 in FIGS. 1A and 1B. The difference is that the guide tubes 184 and 186 have the integrated handle region 182 that provides the thickness corresponding to the flange 32 of the guide tube 30. In other words, in FIGS. 1A and 1B, the flange 32 could be extended to create a handle, like the handle region 182 that is shown in FIG. 14.

Like the guide tube 30 in FIG. 1, the purpose of the guide tubes 184 and 186 is for mating within the master tube 20 and, once properly seated in the master tube 20, to receive one or more of the drill bits 172 used to create the osteotomy. Because creation of the osteotomy pursuant to the dental plan calls for a sequence of several drill bits 172 having different diameters, the guide-tube tools 180 have different diameters to engage the drill bits 172 in a relatively tight fashion to prevent the drill bit from drilling at the wrong angle. Thus, for each diameter of a drill bit 172, there is a corresponding guide-tube tool 180. Further, because the master tubes 20 may come in different sizes, the guide-tube tools 180 may include guide tubes 184 and 186 having different outer diameters for mating with the different sized mater tubes 20. As an example, the lower two guide-tube tools 180 may only be used with a master tube 20 with a 5.1 mm inner diameter.

Figure 15:
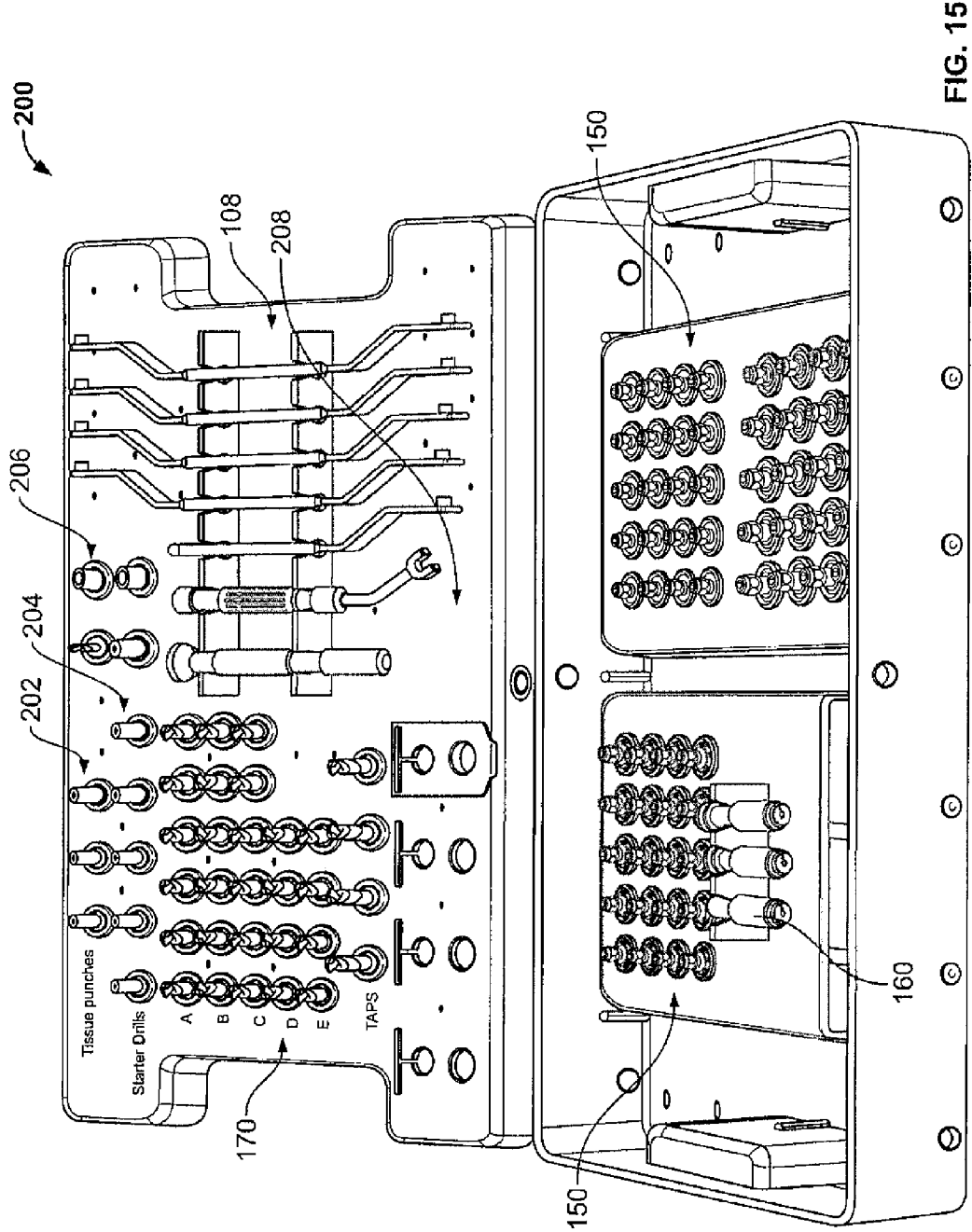
FIG. 15 illustrates a large-scale surgical kit including the various components and kits that are illustrated in FIGS. 12-14.

FIG. 15 illustrates a surgical kit 200 that includes many of the kits previously discussed. The lower portion of the surgical kit 200 includes the kit 150 of implant mounts 40 of various sizes. The lower portion of the surgical kit 200 also includes the bone profilers 160. The upper portion of the surgical kit 200 includes a set 170 of drill bits 172, which may include taps for creating female threads within the osteotomy. The surgical kit 200 also includes the guide-tube tools 180.

The surgical kit 200 further includes tissue punches 202 for removal of a known size of gingival tissue from beneath the openings in the surgical guide 70. The surgical kit 200 also includes starter drills 204, such as drill bits for creating a pilot hole and, possibly, countersinks for creating a certain shape to the opening of the osteotomy. The surgical kit 200 may include other types of tools such as implant holders 206 for holding the implants 10 as they are mated 48 (FIG. 3) of the implant mount 40. The surgical kit 200 is preferably made of any material that allows it to be sterilized via an autoclave.

FIGS. 16-21 provide a series of illustrations in which the surgical guide 70 is used to place the dental implants 10 within the patient's mouth in accordance with the pre-established dental plan of FIG. 4. As mentioned previously, a surgical guide 70 was created through a technique that allows it to have a negative impression of the gingival surface within the patient's mouth. Accordingly, after it has been developed, the surgical guide 70 can be installed into the patient's mouth such that it fits snugly over the gingival tissue or teeth or bone. The surgical guide 70 is held in place in the patient's mouth by use of small, temporary fixations screws or pins that fit through the openings 74 in the surgical guide 70. Once it is fixed in place, the surgical guide 70 is used to conduct surgery in accordance to the dental plan discussed with respect to FIG. 4.

Figure 16:
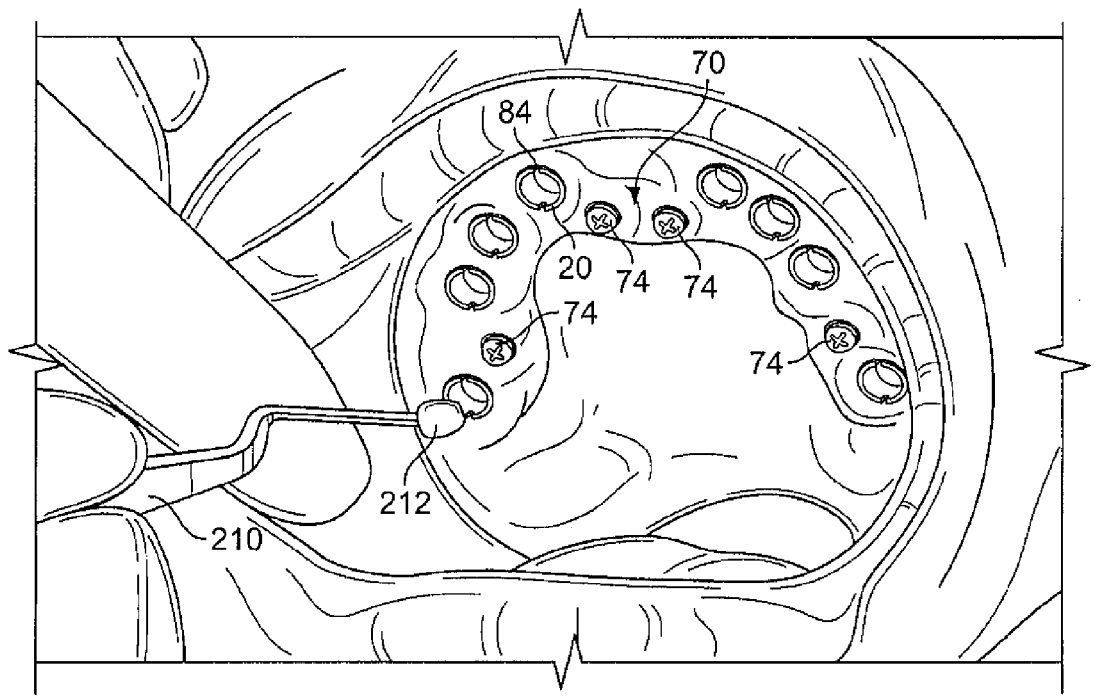
FIG. 16 illustrates the surgical guide fixed in the patient's mouth, as a portion of the gingival tissue is being removed before developing an osteotomy in the patient's mouth.

FIG. 16 illustrates a tool 210 grasping a piece of gingival tissue 212 that has been cut using one of the tissue punches 202 (FIG. 15) inserted through the master tube 20. Similarly, pieces of the gingival tissue are removed from each of the eight openings defined by the master tubes 20 to expose the underlying bone.

Figure 17:
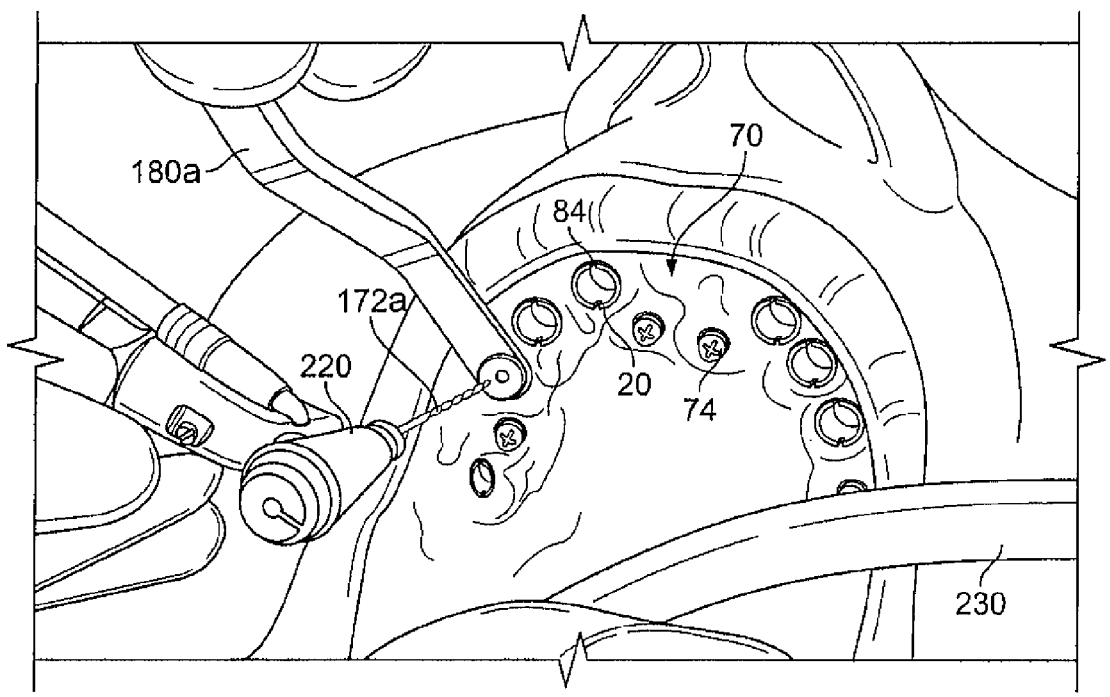
FIG. 17 illustrates one of the guide-tube tools being placed in the master tube within the surgical guide when the surgical guide is placed in the patient's mouth.

FIG. 17 illustrates the use of a certain guide-tube tool 180a that fits within one of the master tubes 20. The guide-tube tool 180a then receives a first drill bit 172a (for example, a pilot drill) that is powered by a driver 220. Because of the various fluids and materials that can build up during the surgery within patient's mouth, a suction tube 230 is often employed.

Figure 18:
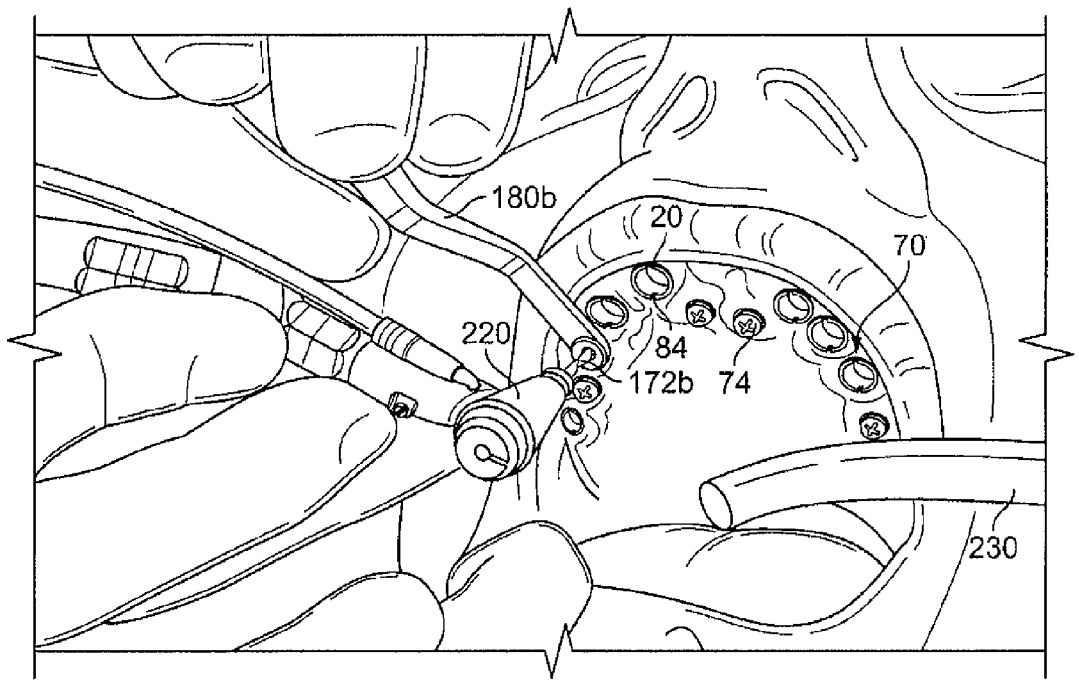
FIG. 18 illustrates one of the drill bits being guided by the guide-tube tool when the surgical guide is placed in the patient's mouth.

FIG. 18 illustrates the use of a second guide-tube tool 180b that fits within the same master tube 20. The second guide-tube tool 180b then receives a slightly larger drill bit 172b to enlarge the opening in the bone created by the first drill bit 172a. Each of the master tubes 20 receives a certain sequence of guide-tube tools 182 and drill bits 172 to create an osteotomy with a known size and shape in accordance with the dental plan that has been determined for that patient. Thus, the clinician is given a set of instructions, in accordance to the dental plan, for developing each opening in the bone with a specific sequence of guide-tube tools 182 and drill bits 172.

Figure 19:
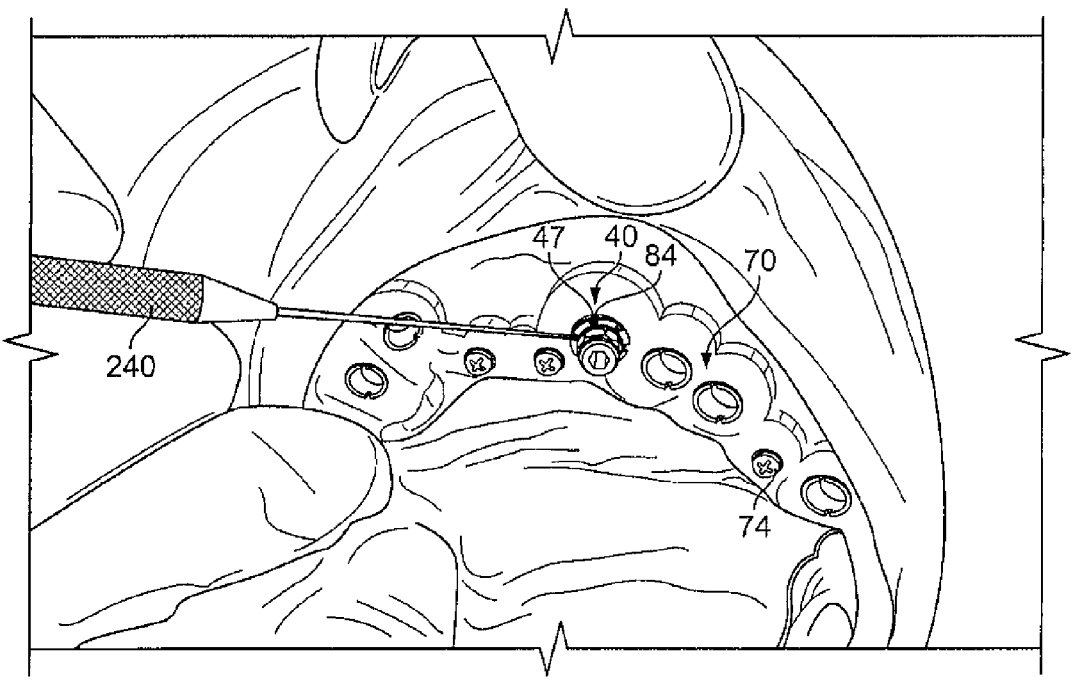
FIG. 19 illustrates the first of eight dental implants and associated implant mounts being placed in the osteotomy after receiving depth, angulation, and angular orientation guidance from the surgical guide and integrated master tubes.

FIG. 19 illustrates the placement of one of the dental implants 10, which has been attached to a specifically-sized implant mount 40 in accordance to the plan. In particular, the implant 10 has been screwed into the bone by use of a tool that engages the driving element 48 of the implant mount 40. Because the underlying non-rotational feature 12 of the implant 10 (FIG. 1) is aligned with the notch 47, the non-rotational feature 12 is oriented in the exact location defined by the dental plan by aligning the notch 47 of the implant mount 40 with the notch 84 in the master tube 20. As discussed previously, because the implant mount 40 has a known length, the exact depth of the implant 10 within the osteotomy is also known, as defined by the dental plan for that patient.

Figure 20:
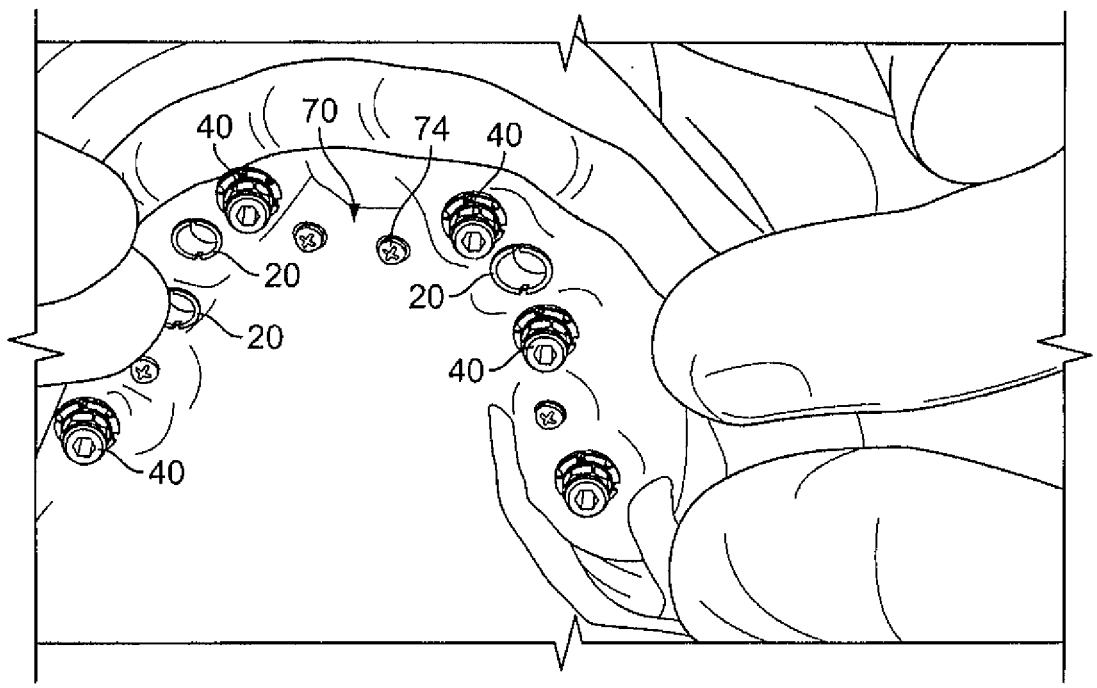
FIG. 20 illustrates several of dental implants and implant mounts after placement in their respective osteotomies by use of the surgical guide.
Figure 21:
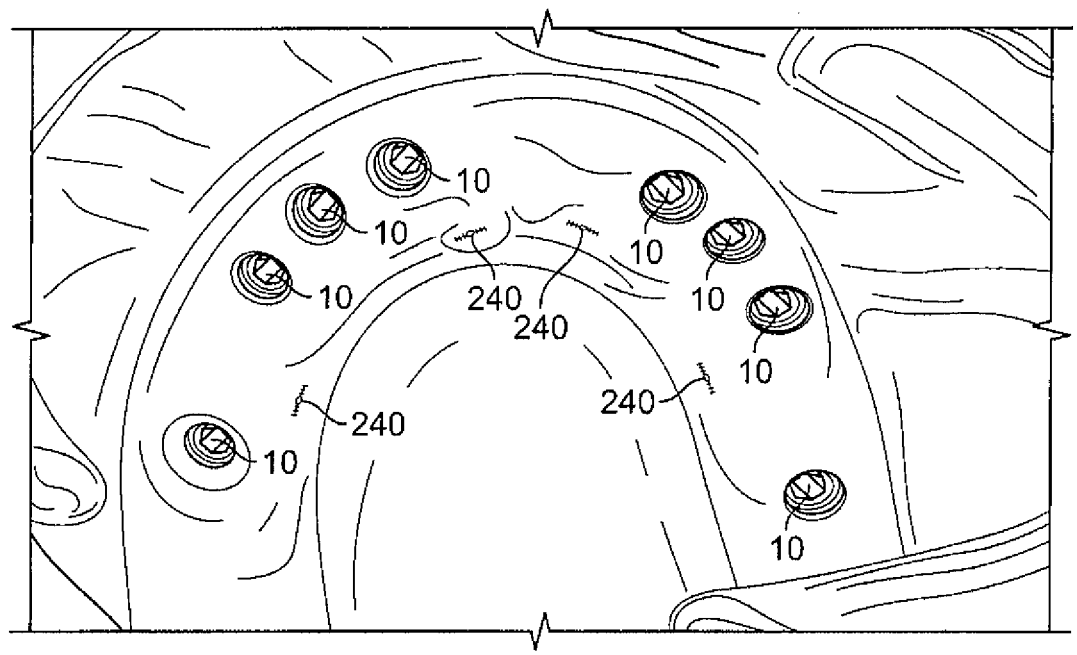
FIG. 21 illustrates all eight dental implants in the respective osteotomies after the surgical guide has been removed from the patient's mouth.

FIG. 20 illustrates several implants 10 that have been installed by use of the implants mounts 40 passing through their respective master tubes 20 of the surgical guide 70. Once all of the implants 10 are installed or after each implant is installed, the implant mounts 40 can be released from the dental implants 10 can by unscrewing each of the screws 49 (FIGS. 2-3). Additionally, the surgical guide 70 can be removed from the patient's mouth by removal of the temporary fixation screws or pins from the holes 74 in the surgical guide 70. As shown best in FIG. 21, the implants 10 are located within well-defined holes in the patient's gingival tissue. Further, the patient may receive sutures 240 in the gingival tissue in the regions where the temporary fixation screws or pins had been inserted into the patient's bone.

Because each of the implants 10 are at known locations and have known orientations defined by the surgical guide 70 in accordance with the dental plan, the patient can be immediately fitted with a prosthesis that was previously made in accordance to the dental plan. As an example, the bar structure 135 that was made from the stone model 131 in FIG. 10B be can be placed on the implants 10 in the patient's mouth. The eight attachment regions 137 of the bar 135 will fit accurately on the dental implants 10 and can be coupled to the dental implants 10 through typical dentals screw. A temporary or final denture can then be snapped on the bar structure 135 such that the patient now has a workable set of prosthetic teeth that are defined by the dental plan.

In summary, by using a surgical guide 70 having the master tubes 20 that allow for the known orientation of the non-rotational features 12, 108 of the implants 10 and the implant analogs 120, a stone model 131 can be accurately developed to replicate the desired conditions in the patient's mouth in accordance with the dental plan. A prosthetic device can be manufactured by use of the stone model 131. The surgical guide 70 can then be fitted to patient's mouth and the implants 10 can be installed in the patient's mouth in substantially the identical location and orientation as the implant analogs 120 in the stone model 131, as defined by the dental plan. The prosthetic device can then be fitted to the implants 10 that have been installed in the patient's mouth.

In summary, by using a surgical guide 70 having the master tubes 20 that allow for the known orientation of the non-rotational features 12, 108 of the implants 10 and the implant analogs 120, a stone model 130 can be accurately developed to replicate the desired conditions in the patient's mouth in accordance with the dental plan. A prosthetic device can be manufactured by use of the stone model 130. The surgical guide 70 can then be fitted to patient's mouth and the implants 10 can be installed in the patient's mouth in substantially the identical location and orientation as the implant analogs 120 in the stone model 130, as defined by the dental plan. The prosthetic device can then be fitted to the implants 10 that have been installed in the patient's mouth.

It should be noted that while the surgical guide 70 has been described as being developed through a dental scan (e.g., CT scan) of the patient's mouth, the surgical guide 70 can be developed by other common techniques involving the use of impression material within the patient's mouth and/or stone models created by the impression material, which is often referred to as model-based surgery.

Further, while the present invention has been described relative to the use of a dental plan to create a denture-type prosthetic device, the present invention is also useful for developing and installing one or more single tooth prosthetic devices, or one or more multi-tooth prosthetic devices in a patient. In other words, the surgical guide 70 may be smaller such that it only covers a limited portion of the dental arch.

Also, it should be noted that the surgical guide 70 can be used directly in the surgical stage without being used to create a prosthesis via the stone model. In other words, the surgical guide 70 can be developed via the scan of the patient's mouth in accordance to a dental plan. Once the surgical guide 70 is placed in the patient's mouth, the implants 10 can be installed in the bone at the locations corresponding to the dental plan with the drill bits 172 and the guide-tube tools 180 (along with other components and tools described above). Further, it is often important to align the non-rotational feature 12 of the implants 10 such that a flat surface of the non-rotational feature 12 is substantially parallel to the buccal side of the dental arch. Thus, the master tubes 20 are accurately positioned in the surgical guide 70 so that the notches 84 dictate the placement of the implant 10 (via the implant analog 40) at a location that results in the flat surface of the non-rotational feature 12 being substantially parallel to the buccal side of the dental arch. The implants 10 can then be fitted with a temporary prosthesis crafted by the clinician using common abutments. Or, the implants 10 may receive a healing cap or healing abutment to allow for a period of osseointegration before a temporary or final prosthesis is fitted.

Figure 22A:
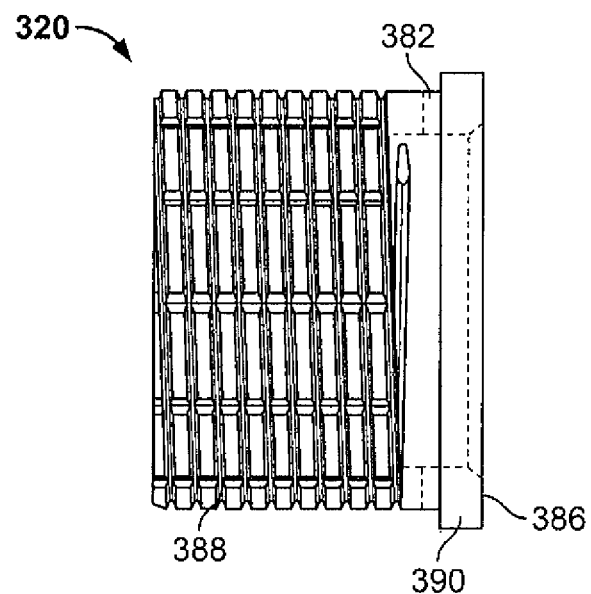
FIG. 22a is a view of an alternative master tube that is placed in the surgical guide of FIG. 5.
Figure 22B:
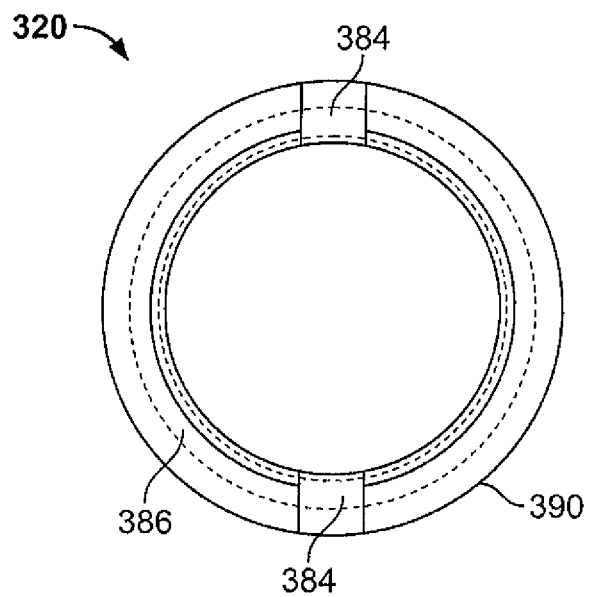
FIG. 22b is another view of the alternative master tube that is placed in the surgical guide of FIG. 5.

FIGS. 22A and 22B illustrate an alternative master tube 320. The master tube 320 serves the same purpose the master tube 20 described above. The master tube 320 includes a main body 382 with notches 384 located on the upper surface 386. The master tube 320 includes a roughened side surface 388 that allows the master tube 320 to be better attached to the material of the surgical guide 70. As shown, the roughened surface 388 includes a spiral groove (or perhaps a knurled surface) around the circumference of the main body 382 and axial grooves along the central axis of the main body 382 that intersect the spiral grooves. Unlike the previous master tube 20, the master tube 320 of FIGS. 22A and 22B includes a flange 390 at the upper surface 386 that allows it to be axially retained in the surgical guide 70 with better precision. The undersurface of the flange 390 engages the material of the surgical guide 70, so as to resist any axial movement of the master tube 320 relative to the surgical guide 70.

The flange 390 may rest on the top surface of the surgical guide 70 or within a countersunk opening within the top surface of the surgical guide 70. In either case, the dimensions "A", "B", "C", "D", and "E" of FIG. 1B are also applicable to the master tube 320 so as to develop a surgical guide that will place each dental implant 10 in accordance to the dental plan.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims.

What is claimed is:

1. A method of installing a threaded dental implant in a patient's mouth, comprising:
    placing a surgical guide over the gum tissue in the patient's mouth, the surgical guide including an opening for receiving the threaded dental implant;
    inserting the threaded dental implant into the opening by applying rotational force to the threaded dental implant; and
    stopping the insertion in response to a non-rotational feature on the threaded dental implant being aligned with at least one indicia along the opening such that the non-rotational feature is at a known position within the opening.

2. The method of claim 1, wherein the inserting includes applying torque to an implant mount to which the threaded dental implant is attached.

3. The method of claim 2, wherein the implant mount has a mount-rotational feature that is aligned with the at least one indicia upon the stopping of the insertion of the threaded dental implant.

4. The method of claim 3, wherein the at least one indicia is located on a master tube that is present in the surgical guide.

5. The method of claim 4, wherein the at least one indicia is at least one notch located in the master tube, and the implant mount has corresponding notches for alignment with the at least one notch on the master tube.

6. The method of claim 1, wherein the at least one indicia along the opening is a plurality of indicia.

7. A method of manufacturing a dental prosthesis for placement in a patient's mouth, comprising:
    developing a surgical guide to be used in the placement of at least one threaded dental implant at a predetermined location in the patient's mouth, the surgical guide fitting over the tissue and including an opening and a marker adjacent to the opening, the marker for alignment with a non-rotational feature of the at least one threaded dental implant, the opening being configured to rotationally engage an implant mount having the threaded dental implant coupled thereto, the implant mount having implant-mount indicia for alignment with a corresponding surface of the non-rotational feature of the threaded dental implant and with the marker, at least one of the marker and the implant-mount indicia being a plurality thereof;
    developing a model of the patient's mouth using the surgical guide; and
    developing the dental prosthesis on the model, the dental prosthesis including a mating structure for mating with the non-rotational feature of the at least one threaded dental implant;
    wherein the surgical guide is configured to be placed in the patient's mouth such that the at least one threaded dental implant may be installed through the opening in the surgical guide by applying rotational force to the implant mount, the at least one threaded dental implant being installed such that, in response to the implant-mount indicia being aligned with the marker during installation of the threaded dental implant, the non-rotational feature is at a known angular orientation with respect to the marker and such that a dental prosthesis may be attached thereto.

8. The method of claim 7, wherein the surgical guide includes a master tube that includes a notch for providing the marker.

9. The method of claim 8, wherein the surgical guide is made of a polymeric material and the master tube is made from a metal, the master tube being embedded in the polymeric material.

10. The method of claim 8, wherein the developing the model includes using a dental implant analog within the model to replicate the position of the threaded dental implant, the dental implant analog including an analog non-rotational feature replicating the non-rotational feature of the threaded dental implant, the analog non-rotational feature being aligned with the marker on the surgical guide.

11. The method of claim 8, wherein a plurality of drill bits that fit through the opening is configured to be used in developing an osteotomy prior to the installation of the dental implant.

12. The method of claim 11, wherein a plurality of different sized guide tubes is configured to be mated with the master tube and to be used during the developing an osteotomy with the plurality of drill bits.

13. The method of claim 7, wherein the dental prosthesis includes a dental bar that includes the mating structures for mating with the implant analogs in the model and with the implants in the patient's mouth.

14. A method of making a dental prosthesis for placement in a patient's mouth, comprising:
    developing a surgical guide to be used in the placement of at least one dental implant at a predetermined location in the patient's mouth, the surgical guide fitting over the gingival surface of the patient's mouth and including at least one opening for installing the at least one dental implant therethrough;
    by use of the surgical guide, developing a model of the patient's mouth, the model including at least one implant analog that is positioned within the model at a location and orientation corresponding to the desired location and orientation of the at least one dental implant to be placed in the patient's mouth; and
    using the model to develop the dental prosthesis,
    wherein developing the model includes holding the at least one implant analog in place relative to the surgical guide while material is being poured into the surgical guide to develop the model.

15. The method of claim 14, wherein the predetermined location of the at least one dental implant to be placed in the patient's mouth is obtained from at least one scan of the patient's mouth to obtain hard tissue data and gingival tissue data.

16. The method of claim 15, wherein the hard tissue data is obtained using a CT-scanner.

17. The method of claim 15, further comprising using data obtained from the scanning to create a predefined prosthetic abutment to be attached to the at least one dental implant, wherein the predefined prosthetic abutment is a part of the dental prosthesis.

18. The method of claim 14, wherein the surgical guide further includes a plurality of openings through which temporary fixation elements may be placed for holding the surgical guide in the proper location on the gingival surface.

19. The method of claim 14, wherein the at least one implant analog includes an upper surface that replicates the upper surface of the dental implant to be placed in the patient's mouth.

20. The method of claim 19, wherein the dental implant analog includes an analog non-rotational feature replicating a non-rotational feature of the at least one dental implant.

21. The method of claim 14, wherein the surgical guide includes at least one master tube embedded therein, the at least one master tube defining the at least one opening.

22. The method of claim 21, wherein the act of developing a model of the patient's mouth using the surgical guide includes inserting at least one implant-analog mount through the at least one master tube, the at least one implant analog being attached to a lower portion of the at least one implant-analog mount.

23. The method of claim 14, further comprising, by use of the surgical guide, placing the dental implant at the desired location and orientation in the patient's mouth.

24. The method of claim 23, further comprising attaching the dental prosthesis to the dental implant after the dental implant has been placed in the patient's mouth.

25. A method of making a dental prosthesis for placement in a patient's mouth, comprising:
developing a surgical guide to be used in the placement of at least one dental implant at a predetermined location in the patient's mouth, the surgical guide fitting over the gingival surface of the patient's mouth and including at least one opening for installing the at least one dental implant therethrough;
by use of the surgical guide, developing a model of the patient's mouth, the model including at least one implant analog that is positioned within the model at a location and orientation corresponding to the desired location and orientation of the at least one dental implant to be placed in the patient's mouth;
using the model to develop the dental prosthesis;
locking an upper, expandable portion of an implant-analog mount into the at least one opening for maintaining the position of the attached implant analog relative to the surgical guide;
after the at least one implant-analog mount is locked into the at least one opening, pouring a stone material into a backside of the surgical guide; and
after the stone material has hardened, unlocking the at least one implant-analog mount from the at least one opening to release the at least one implant analog such that the at least one implant-analog mount can be removed from the surgical guide.

26. The method of claim 25, further comprising, by use of the surgical guide, placing the dental implant at the desired location and orientation in the patient's mouth.

27. The method of claim 26, further comprising attaching the dental prosthesis to the dental implant after the dental implant has been placed in the patient's mouth.

28. A method of making a dental prosthesis for placement in a patient's mouth, comprising:
receiving a dental plan based on at least one scan of the patient's mouth to obtain hard tissue data and gingival tissue data, the dental plan including the location of at least one threaded dental implant;
developing a surgical guide based on the dental plan, the surgical guide configured to be used in the rotational placement of the at least one threaded dental implant in the patient's mouth, the threaded dental implant having a non-rotational feature, the surgical guide fitting over tissue of the gingival surface of the patient's mouth and including at least one opening for installing the at least one threaded dental implant therethrough, the surgical guide including a marker adjacent the at least one opening, the at least one opening being configured to rotationally engage an implant mount having the threaded dental implant coupled thereto, the implant mount having implant-mount indicia for alignment with a corresponding surface of a non-rotational feature of the at least one threaded dental implant and with the marker such that when the implant-mount indicia is aligned with the marker during installation of the threaded dental implant, the non-rotational feature is at a known angular orientation with respect to the marker, at least one of the marker and the implant-mount indicia being a plurality thereof;
by use of the surgical guide, developing a model of the patient's mouth, the model including at least one implant analog that is positioned within the model at a location and orientation that corresponds to the desired location and orientation of the at least one threaded dental implant to be placed in the patient's mouth; and
using the model to develop the dental prosthesis to be secured to the at least one threaded dental implant in the patient's mouth.

29. The method of claim 28, further comprising using data obtained from the scanning to create a predefined prosthetic abutment to be attached to the at least one dental implant, wherein the predefined prosthetic abutment is a part of the dental prosthesis.

30. The method of claim 28, wherein the at least one implant analog includes an upper surface that replicates the upper surface of the dental implant to be placed in the patient's mouth.

31. The method of claim 30, wherein the dental implant analog includes an analog non-rotational feature replicating the non-rotational feature of the at least one dental implant.

32. The method of claim 28, wherein the surgical guide includes at least one master tube embedded therein, the at least one master tube defining the at least one opening.

33. The method of claim 32, wherein the act of developing a model of the patient's mouth using the surgical guide includes inserting at least one implant-analog mount through the at least one master tube, the at least one implant analog being attached to a lower portion of the at least one implant-analog mount.

34. The method of claim 33, further comprising locking an upper, expandable portion of the implant-analog mount into the at least one master tube for maintaining the position of the attached implant analog relative to the surgical guide.

35. The method of claim 34, wherein the act of developing a model of the patient's mouth using the surgical guide includes further comprises:
after the at least one implant-analog mount is locked into the at least one master tube, pouring a stone material into a backside of the surgical guide; and
after the stone material has hardened, unlocking the at least one implant-analog mount from the at least one master tube to release the at least one implant analog such that the at least one implant-analog mount can be removed from the surgical guide.

36. The method of claim 28, wherein the hard tissue data is obtained using a CT-scanner.

37. The method of claim 28, wherein the surgical guide is configured to be used to install the at least one dental implant into the patient's mouth.

* * * * *